(12) United States Patent
Federspiel et al.

(10) Patent No.: US 7,759,104 B2
(45) Date of Patent: Jul. 20, 2010

(54) PARAMYXOVIRIDAE VIRUS PREPARATIONS

(75) Inventors: Mark J. Federspiel, Rochester, MN (US); Troy R. Wegman, Rochester, MN (US); Kirsten K. Langfield, Lake City, MN (US); Henry J. Walker, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 11/995,639

(22) PCT Filed: Jul. 14, 2006

(86) PCT No.: PCT/US2006/027330

§ 371 (c)(1),
(2), (4) Date: May 12, 2008

(87) PCT Pub. No.: WO2007/011711

PCT Pub. Date: Jan. 25, 2007

(65) Prior Publication Data

US 2008/0241930 A1    Oct. 2, 2008

Related U.S. Application Data

(60) Provisional application No. 60/699,254, filed on Jul. 14, 2005.

(51) Int. Cl.
*C12N 7/02* (2006.01)
*A61K 39/165* (2006.01)

(52) U.S. Cl. .................... 435/239; 424/212.1

(58) Field of Classification Search ............ None
See application file for complete search history.

(56) References Cited

U.S. PATENT DOCUMENTS

| | | | |
|---|---|---|---|
| 5,837,520 | A | 11/1998 | Shabram et al. |
| 6,146,873 | A | 11/2000 | Kistner et al. |
| 6,146,891 | A * | 11/2000 | Condon et al. ............. 435/378 |
| 6,210,683 | B1 | 4/2001 | Burke et al. |
| 6,245,549 | B1 | 6/2001 | Ewasyshyn et al. |
| 6,586,411 | B1 | 7/2003 | Russell et al. |
| 6,673,572 | B2 | 1/2004 | Parks et al. |
| 6,855,535 | B2 | 2/2005 | Meyer et al. |
| 7,078,218 | B2 | 7/2006 | Smith |
| 2001/0021385 | A1 | 9/2001 | Volkin |
| 2002/0069421 | A1 | 6/2002 | Hale et al. |
| 2003/0235532 | A1 | 12/2003 | Russell et al. |
| 2004/0009936 | A1 | 1/2004 | Tang et al. |
| 2005/0142148 | A1 | 6/2005 | Fouchier et al. |

FOREIGN PATENT DOCUMENTS

WO    WO 01/13106 A1    2/2001

OTHER PUBLICATIONS

Phuong et al. Cancer Research, 2003, 63:2462-2469.*
Cherny et al., "Site-directed Mutagenesis of the Arginine-Glycine-Aspartic Acid in Vitronectin Abolishes Cell Adhesion," *J. Biol. Chem.*, 1993, 268(13):9725-9729.
Devaux and Cattaneo, "Measles Virus Phosphoprotein Gene Products: Conformational Flexibility of the P/V Protein Amino-Terminal Domain and C Protein Infectivity Factor Function," *J. Virol.*, 2004, 78(21):11632-11640.
Udem, "Measles Virus: Conditions for the Propagation and Purification of Infectious Virus in High Yield," *J. Virol. Meth.*, 1984, 8:123-136.

* cited by examiner

*Primary Examiner*—Stacy B Chen
(74) *Attorney, Agent, or Firm*—Fish & Richardson P.C.

(57) ABSTRACT

This document involves methods and materials related to obtaining Paramyxoviridae virus preparations.

14 Claims, 3 Drawing Sheets

OVERVIEW OF THE MV-CEA MVB MANUFACTURING PROTOCOL

Cell Thaw and Cell Expansion
Thaw African green monkey Vero cells and seed growth vessels.
Expand cells until sufficient number of cells are obtained.
Seed Cell Factory-10 vessels (CF10s) and follow cell growth until ~80% confluence.

↓

Infect Production System
Infect CF10s with MV-CEA at multiplicity of infection of 0.1 $TCID_{50}$/cell.
Follow cytopathic effect of virus until cells are ≥90% syncytia.

↓

Harvest Production System
Wash cells with PBS, release cells from CF10s with magnesium/EDTA, collect cells
by centrifugation. Resuspend the cell pellet with 40 ml buffer (serum-free media)
per CF10, and snap-freeze the cell suspension.
Perform three cycles of freezing/thawing the cell pellet to release virions.

↓

Clarify Cell Lysate
Centrifuge to remove cell debris and collect cell lysate.

↓

MV-CEA MVB Bulk Product
Pool the clarified cell lysates.
Remove aliquots of product for MV-CEA MVB Bulk Product testing.

↓

Final Filling
Fill vials and store at -80 C.
Remove aliquots of product for MV-CEA MVB Vialed Product testing.

Figure 2

PARAMYXOVIRIDAE VIRUS PREPARATIONS

CROSS-REFERENCE TO RELATED APPLICATIONS

This application is a National Stage application under 35 U.S.C. §371 and claims benefit under 35 U.S.C. §119(a) of International Application No. PCT/US2006/027330 having an International Filing Date of Jul. 14, 2006, which claims the benefit of priority of U.S. Provisional Application Ser. No. 60/699,254, having a filing date of Jul. 14, 2005.

BACKGROUND

1. Technical Field

This document relates to methods and materials involved in obtaining Paramyxoviridae virus preparations.

2. Background Information

Paramyxoviridae viruses are a family of enveloped viruses having an anti-sense single-stranded RNA genome. The viruses within this family have a genome ranging from about 15 to 19 kilobases, which contains between 6 to 10 genes. Infection of host cells occurs when the F protein of a virus particle induces fusion of the cell membrane and viral envelope. Many members of the Paramyxoviridae virus family, including measles virus, cause infected cells to fuse together to form syncytia.

SUMMARY

The present document relates to methods and materials involved in Paramyxoviridae virus preparations and the production of Paramyxoviridae virus preparations. For example, this document provides methods and materials that can be used to obtain large volume, high titer, high purity preparations of Paramyxoviridae viruses (e.g., measles virus; MV) with levels of contaminants in compliance with federal regulations (e.g., levels that are acceptable to the Food and Drug Administration). Methods and materials described herein may be used, for example, to produce clinical quality Paramyxoviridae virus from cells (e.g., Vero cell cultures). Such preparations can have broad uses in research, development, and medical fields. For example, such preparations can allow medical professionals to deliver efficiently large quantities of Paramyxoviridae virus to patients for various clinical treatments (e.g., in virotherapy of cancer).

This document also involves methods and materials for collecting enveloped viruses (e.g., MV) without disrupting their viral envelopes. These methods and materials can allow viruses to retain their ability to infect host cells. Viruses can be collected from infected cells and effectively separated from the cells and cellular materials. The methods and materials provided herein can be used to process a large number of cells and/or a large volume of cell supernatants such that large quantities of Paramyxoviridae viruses are collected. In some embodiments, the compositions provided herein can be sterile. For example, each step of a method used to make a virus preparation can be performed under sterile conditions. In some embodiments, good manufacturing practices (GMP) can be used to make the virus preparations provided herein.

In general, this document features a composition containing Paramyxoviridae virus, wherein the composition has a volume greater than 300 mL and a Paramyxoviridae virus titer greater than $10^6$ $TCID_{50}$ per mL, and wherein the composition is free of bovine serum albumin. The composition can be sterile. The volume can be greater than 500 mL. The Paramyxoviridae virus can be a Morbillivirus virus. The Paramyxoviridae virus can be from a class of viruses selected from the group consisting of measles and mumps viruses. The Paramyxoviridae virus can contain a nucleic acid sequence that encodes a polypeptide, wherein the polypeptide is heterologous to the virus. The polypeptide can contain an amino acid sequence present in human carcinoembryonic antigen, the amino acid sequence being at least ten amino acid residues in length. The polypeptide can contain an amino acid sequence present in a human sodium iodide transporter, the amino acid sequence being at least ten amino acid residues in length. The volume of the composition can be between 20 mL and 100 L. The volume of the composition can be between 10 L and 100 L. The volume of the composition can be between 50 L and 100 L. The Paramyxoviridae virus titer can be between $10^6$ $TCID_{50}$ per mL and $10^{15}$ $TCID_{50}$ per mL. The Paramyxoviridae virus titer can be between $10^9$ $TCID_{50}$ per mL and $10^{15}$ $TCID_{50}$ per mL. The Paramyxoviridae virus titer can be between $10^{12}$ $TCID_{50}$ per mL and $10^{15}$ $TCID_{50}$ per mL. The composition can contain less than 1 mg total protein per mL. The composition can contain less than 750 µg total protein per mL. The composition can contain less than 1 µg of DNA per mL. The composition can contain less than 100 ng of DNA per mL. The maximum length of the non-viral DNA of the composition can be less than 500 bp. The maximum length of the non-viral DNA of the composition can be less than 200 bp.

In another aspect, this document features a composition containing Paramyxoviridae virus, wherein the composition is free of bovine serum albumin, and wherein the virus contains a nucleic acid sequence that encodes a polypeptide, wherein the polypeptide is heterologous to the virus.

In another aspect, this document features a method for making a composition containing Paramyxoviridae virus, wherein the composition has a volume greater than 300 mL and a Paramyxoviridae virus titer greater than $10^6$ $TCID_{50}$ per mL, the method containing (a) obtaining a sample of Paramyxoviridae virus in serum-free medium, and (b) obtaining Paramyxoviridae virus from the sample to form the composition. The serum-free medium can have a volume between 20 mL and 200 L. The serum-free medium can have a volume between 30 L and 200 L. The serum-free medium can have a volume between 60 L and 200 L. The composition can have a Paramyxoviridae virus titer between $10^6$ $TCID_{50}$ per mL and $10^{15}$ $TCID_{50}$ per mL. The composition can have a Paramyxoviridae virus titer between $10^9$ $TCID_{50}$ per mL and $10^{15}$ $TCID_{50}$ per mL. The virus in step (a) can be replicated in a cell selected from the group consisting of a Vero cell, Vero-αHis cell, HeLa cell, HeLa-S3 cell, 293 cell, PC12 cell, CHO cell, 3T3 cell, or a combination thereof. The virus in step (a) can be replicated in a Vero cell. The cell can be cultured in a multi-layered dish. The cell can be cultured in a microcarrier. The cell can be cultured at a temperature between about 30° C. and about 33° C. The method can include, after step (a), contacting the sample with an enzyme. The enzyme can be an endonuclease. The step (b) can include performing a filtering step to remove the Paramyxoviridae virus from a non-Paramyxoviridae component in the sample. The step (b) can include a tangential flow filtering step. The step (b) can include a diafiltering step.

In another aspect, this document features a method for making a composition containing Paramyxoviridae virus, wherein the composition has a volume greater than 300 mL and a Paramyxoviridae virus titer greater than $10^6$ $TCID_{50}$ per mL. The method includes (a) obtaining a sample containing a cell exposed to Paramyxoviridae virus at a multiplicity of infection less than 1 per cell; and (b) obtaining Paramyxoviridae virus from the sample to form the composition.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2 is a flowchart summarizing steps that can be used to produce a Paramyxoviridae virus preparation that can be maintained as a master virus bank.

DETAILED DESCRIPTION

Figure 1:
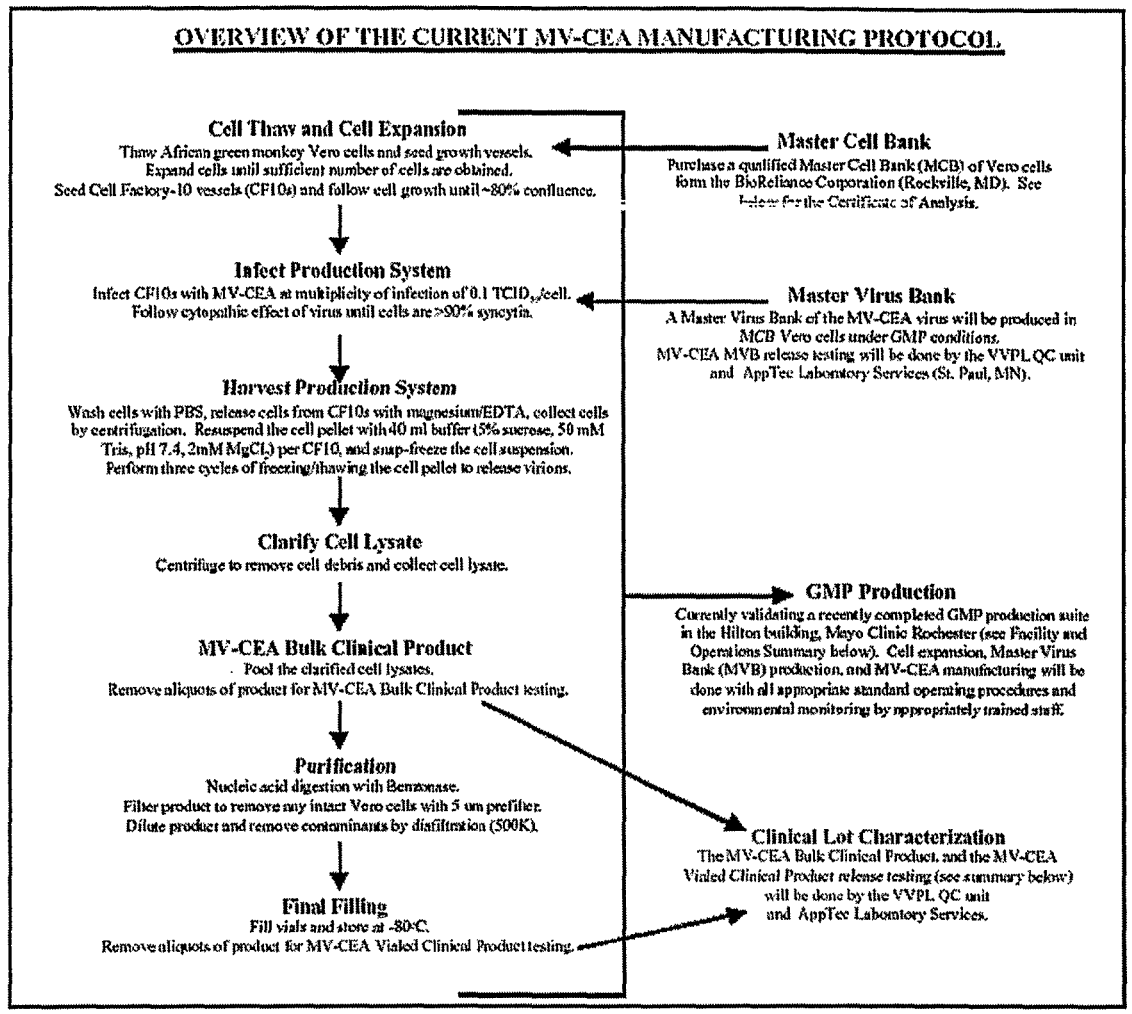
FIG. 1 is a flowchart summarizing steps that can be used to produce a Paramyxoviridae virus preparation.
Figure 3:
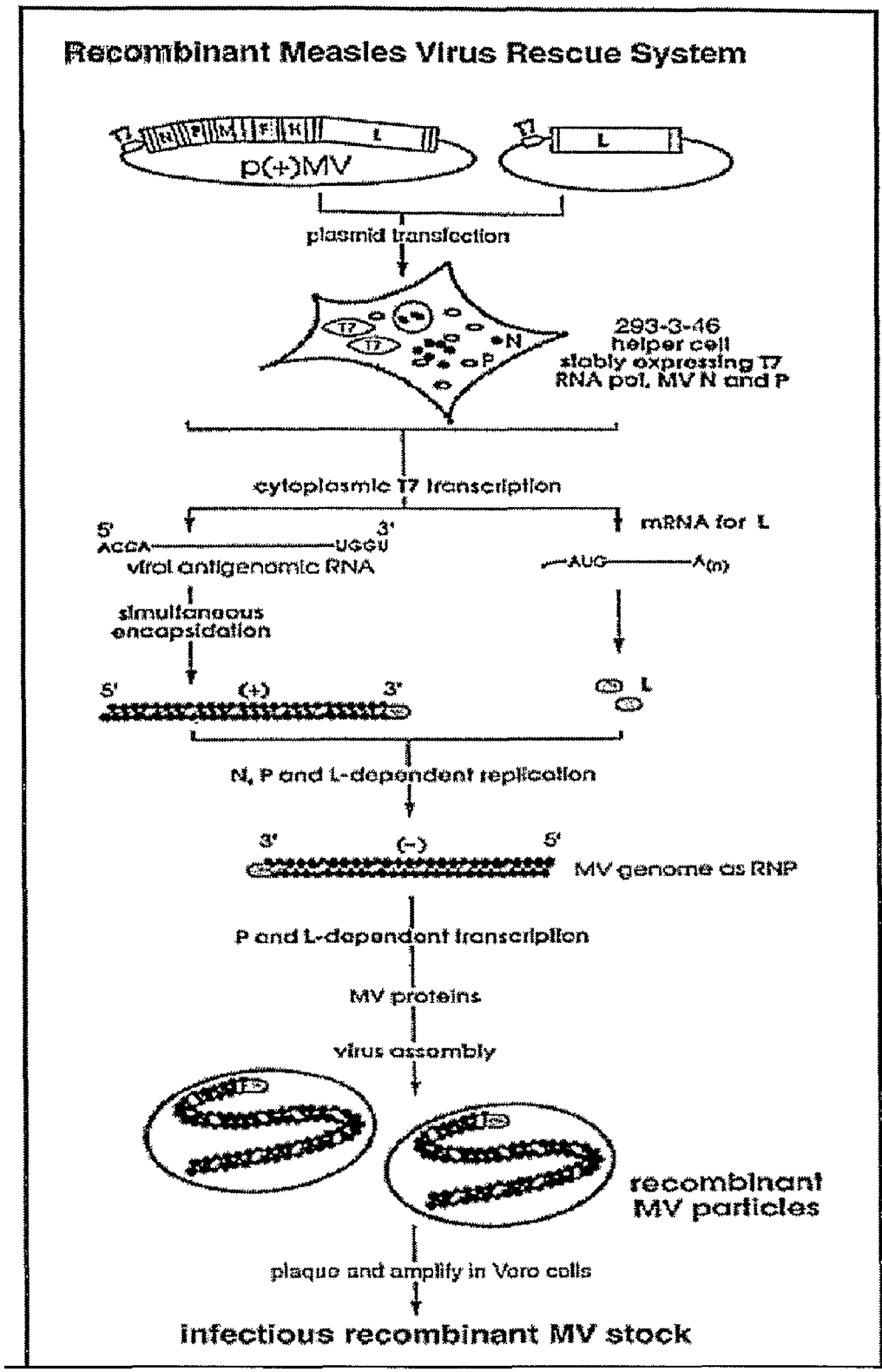
FIG. 3 is a diagram outlining a recombinant measles virus rescue system.

This document provides methods and materials related to producing Paramyxoviridae virus preparations. The Paramyxoviridae virus preparations can be large volume, high titer preparations of Paramyxoviridae virus. The preparations can be purified such that the Paramyxoviridae virus preparation is substantially free of non-viral polypeptides and host cell DNA. In some cases, a preparation can contain DNA. Such DNA can be treated such that most, if not all (e.g., at least 80, 85, 90, 95, or 99 percent), is less than 500 bp (e.g., less than 450, 400, 350, 300, 250, 200, 150, 100 bp) in length.

The preparations can have any volume. For example, the volume can be greater than 1 µL, greater than 1 mL, greater than 500 mL, greater than 1 L, greater than 100 L, greater than 1000 L, or greater than 10,000 L. In some embodiments, the volume can be less than 10,000 L, less than 1000 L, less than 100 L, less than 1 L, or less than 1 mL. In some embodiments, the preparation can have a volume that ranges from about 5 mL to about 500 L (e.g., from about 10 mL to about 250 mL, from about 25 mL to about 200 L, from about 50 mL to about 100 L, from about 300 ml to about 50 L, or from about 300 mL to about 25 L).

The preparation can have a Paramyxoviridae virus titer that is, for example, greater than $10^1$, $10^2$, $10^3$, $10^4$, $10^5$, $10^6$, $10^7$, $10^8$, $10^9$, $10^{11}$, or $10^{12}$ $TCID_{50}$ per mL. In some embodiments, the titer can be less than $10^{12}$, $10^{11}$, $10^{10}$, $10^9$, $10^8$, $10^7$, $10^5$, $10^4$, or $10^3$ $TCID_{50}$ per mL. It follows that the titer can also be between any of these concentrations. For example, the titer can be between $10^5$ and $10^7$ $TCID_{50}$ per mL, between $10^5$ and $10^8$ $TCID_{50}$ per mL, between $10^6$ and $10^{10}$ $TCID_{50}$ per mL, between $10^7$ and $10^{12}$ $TCID_{50}$ per mL, or between $10^2$ and $10^{12}$ $TCID_{50}$.

The preparation can have any concentration of host cell DNA. For example, the preparation can contain less than 1 ng, 20 ng, 100 ng, 500 ng, 1 µg, 20 µg, or 100 µg of host cell DNA per mL. In some embodiments, the concentration of host cell DNA can be between 0 ng per mL and 10 mg per mL, between 2 and 250 ng per mL, between 10 and 300 ng per mL, between 40 and 500 ng per mL, between 500 ng and 5 µg per mL, or between 4 µg and 9 mg per mL. In some embodiments, the preparation can be substantially free of host cell DNA.

The preparation can have any concentration of non-viral polypeptides. For example, the preparation can contain less than 1 ng, 50 ng, 500 ng, 950 ng, 200 µg, 300 µg, 500 µg, 750 µg, or 1 mg of non-viral polypeptides per mL. In some embodiments, the concentration of non-viral polypeptides can range from 1 ng per mL to 10 mg per mL (e.g., from about 5 ng per mL to about 250 ng per mL, from about 500 ng per mL to about 50 µg per mL, or from about 20 ng per mL to about 1 mg per mL). In some embodiments, the preparation can be substantially free of non-viral polypeptides.

The preparation can contain any concentration of actin polypeptides. For example, the preparation can contain less than 1 ng, 20 ng, 100 ng, 500 ng, 1 µg, 20 µg, 100 µg, 1 mg, or 10 mg of actin polypeptides per mL. The concentration of actin polypeptides can be greater than 2 ng, 10 ng, 50 ng, 700 ng, 3 µg, 45 µg, or 900 µg per mL. The concentration of actin polypeptides can be between 0 ng per mL and 10 mg per mL (e.g., between about 2 and 250 ng per mL, between about 10 and 300 ng per mL, between about 40 and 500 ng per mL, between about 500 ng and 5 µg per mL, or between about 4 µg and 9 mg per mL). In some embodiments, the preparation can be substantially free of actin polypeptides.

The viruses in a Paramyxoviridae preparation can be any type of Paramyxoviridae virus. For example, the preparation can contain measles virus, mumps virus, respiratory syncytial virus, canine distemper virus, parainfluenza virus, Newcastle disease virus, simian virus 5, rinderpest virus, or any other type of Paramyxoviridae virus. The preparation can contain any combination of two or more types of Paramyxoviridae viruses (e.g., the preparation can contain measles virus and mumps virus; measles virus and respiratory syncytial virus; parainfluenza virus, simian virus 5, and rinderpest virus; or Newcastle disease virus, mumps virus, and parainfluenza virus).

In some embodiments, the Paramyxoviridae virus can have a wild-type genome. In some embodiment, the preparation can contain genetically modified Paramyxoviridae virus. The genetically modified Paramyxoviridae virus can have any nucleic acid sequence. For example, the Paramyxoviridae virus can have a hybrid genome, partially deleted genome, a genome with one or more point mutations, or a recombinant genome. A Paramyxoviridae virus having a partially deleted genome can have any segment of its genome deleted. In one embodiment, there can be complete or partial deletions of a Paramyxoviridae virus's N, P, C, V, M, F, H, or L genes, or any other sequence found in a Paramyxoviridae virus genome. A Paramyxoviridae virus having one or more point mutations can have one or more nucleic acids inserted, deleted, or substituted at any position in its genome. For example, there can be one or more point mutations in a Paramyxoviridae virus's N, P, C, V, M, F, H, or L genes, or any other sequence found in a Paramyxoviridae virus genome. In one embodiment, an alanine substitution can be made at residues 481 and 533 of the H protein. In some embodiments, tyrosine substitutions can be made at residues 324, 388, and 502 of the N protein, histidine substitutions can be made at residues 97 and 486 of the F protein; and a glycine substitution can be made at residue 2,103 of the L protein.

A recombinant genome can contain any nucleic acid sequence. For example, it can have one or more heterologous sequences at the 5' end, the 3' end, or anywhere between the 5' and 3' ends. A recombinant Paramyxoviridae virus genome can encode one or more antigens, tags, or non-viral polypeptides. For example, a recombinant Paramyxoviridae virus genome can contain nucleic acid encoding a human carcinoembryonic antigen, a human sodium iodide transporter polypeptide, or both.

The Paramyxoviridae preparation can contain one or more types of genetically modified or unmodified virus. For example, a preparation can contain two, three, four, five, six, or more genetically modified Paramyxoviridae viruses or unmodified viruses.

Any method can be used to make a Paramyxoviridae virus preparation. For example, the methods provided herein can be used to make a Paramyxoviridae virus preparation having a high titer, large volume, high degree of purity. The viruses of such preparations can have stable envelopes. Typically, the preparation can be made by first infecting cells with a Paramyxiviridae virus at a low multiplicity of infection (MOI). However, any MOI can be used. For example, a MOI less than about 0.01, 0.1, 0.5, 1.0, 2.0, 20, or 50 viruses per cell can be used. An MOI greater than 0.001, 0.1, 0.5, 1.0, 2.0, 20, or 50 viruses per cell also can be used. In some embodiments, an MOI between about 0.01 and 50 viruses per cell can be used (e.g., an MOI between about 0.01 and 1 virus per cell, an MOI between about 0.5 and 10 viruses per cell, or an MOI between about 1 and 50 viruses per cell). The Paramyxoviridae virus used to infect the cells can come from any source. In some embodiments, Paramyxoviridae viruses can be rescued from a plasmid DNA molecular clone. In another embodiment, Paramyxoviridae viruses can be from virus seed stock, a virus bank, a clinical quality virus preparation, inoculated medium, supernatant from an infected cell culture, an infected cell, or an infected syncytia of cells.

Any type of cell can be infected with a Paramyxoviridae virus in order to replicate virus. For example, Vero cells, Vero-αHis cells, HeLa cells, HeLa-S3 cells, 293 cells, PC12 cells, CHO cells, 3T3 cells, or combinations thereof can be used. In some cases, wild-type or genetically modified cells can be used. For example, untransfected, transiently transfected, or stably transfected cells can be infected with Paramyxoviridae virus.

Following infection, the cells can be cultured under any condition for any length of time. In some embodiments, the cells can be cultured for more than 1 hour, 1 day, 2 days, 3 days, 4 days, 5 days, one week, two weeks, or one month. The cells can be cultured in any culture container (e.g., dishes, multi-well dishes, plates, flasks, microcarriers, roller bottles, or tubes). The cells can be cultured at any temperature between about 27° C. and 39° C. For example, the cells can be cultured between about 27° C. and 37° C., between about 27° C. and 30° C., between about 29° C. and 32° C., or between about 30° C. and 37° C. The cells can be cultured at any concentration of $CO_2$. For example, the cells can be cultured at less than 0.1, 0.5, 1.0, 3.0, 6.0, or 20 percent $CO_2$. In some embodiments, the cells can be cultured at greater than 0.1, 0.5, 1.0, 3.0, 6.0, or 20 percent $CO_2$. In some embodiments, the cells can be cultured between 0 and 15 percent $CO_2$ (e.g., between about 0.1 and 1 percent, between about 0.5 and 10 percent, between about 1 and 16 percent, or between about 5 and 15 percent $CO_2$).

The cells can be cultured in any type of medium. For example, the cells can be cultured in VP-SFM, RPMI, DMEM, OptiMEM, MEM Eagle's, or Hank's BSS. The cells can be cultured in a mixture of two or more types of media. The cells can be cultured with or without serum in the medium. For example, the medium can contain no serum. In some embodiments, the medium can contain less than 0.1, 1, 5, 10, 20, 40, 80, or 100 percent serum. In some embodiments, the medium can contain greater than 0.01, 2, 15, 50, or 90 percent serum. For example, the medium can contain between about 0.001 and 10 percent, between about 0.5 and 60 percent, between about 1 and 85 percent, or between about 20 and 90 percent serum.

After the cells infected with Paramyxoviridae virus are cultured under culture conditions for a desired length of time, any method can be used to collect the Paramyxoviridae viruses. In some embodiments, the viruses can be collected from infected cell lysate or supernatant in which infected cells were grown. Any method can be used to separate Paramyxoviridae viruses from cellular materials contained within a lysate or supernatant. In some embodiments, a lysate or supernatant can be pre-filtered and/or centrifuged. Pre-filtering can be performed using any method of pre-filtering. If the lysate or supernatant is centrifuged, the centrifuge can spin at any force, including greater than 1 g, 10 g, 100 g, 1000 g, 2000 g, 5000 g, 7000 g, 10,000 g, 15,000 g, or 20,000 g. The centrifuge can spin at any temperature (e.g., between about 0.5° C. and 14° C., between about 10° C. and 42° C., between about 12° C. and 29° C., or between about 17° C. and 45° C.).

Once Paramyxoviridae viruses have been separated from cellular materials, some residual cellular DNA and non-viral polypeptides can contaminate the sample containing the Paramyxoviridae viruses. Any method can be used to remove cellular DNA from the sample containing Paramyxoviridae viruses. For example, enzymes can be used to digest the DNA. These enzymes can be any DNA nucleases including, without limitation, endonucleases (e.g., Benzonase®; Merck) or exonucleases. In some cases, the DNA can be digested such that any remaining DNA is less than about 500, 450, 400, 350, 300, 250, 200, 150, or 100 bp in length.

Any method can be used to separate Paramyxoviridae viruses from non-viral polypeptides. For example, a mixture containing viruses can be pre-filtered, filtered, tangential flow filtered, diafiltered, eluted off a column, run through an agarose or acrylamide gel, centrifuged in a sucrose gradient, or separated using any other method.

The invention will be further described in the following examples, which do not limit the scope of the invention described in the claims.

EXAMPLES

Example 1

Paramyxoviridae Virus Stock Preparation

The complete measles virus genome was stored as a molecular clone in plasmid DNA. To rescue infectious viruses from the molecular clone, transgenic helper 293 cells (293-3-46 cells stably expressing T7 polymerase and measles virus N and P proteins) were transfected with the plasmid encoding the measles virus genome. At the same time, the helper 293 cells were also transfected with a helper plasmid coding for the catalytic component of the measles viral polymerase (L protein). Expression of the measles virus genes in both plasmids was driven by a T7 promoter.

MV replication can be controlled by its N, P, and L proteins. The T7 polymerase stably expressed in the helper 293 cells can drove transcription of the L protein encoded on the helper plasmid. Together with the stably expressed N and P proteins, the L protein acted on the transcribed measles virus genome to drive measles virus replication and assembly.

72 hours after transfection, the helper 293 cells were harvested and added to cultures of Vero cells. The Vero cells were cultured at 37° C. at 5% $CO_2$ until plaques formed. The virus was then plaque purified in Vero cells, and amplified for two passages before second and third plaque purifications were performed in Vero cells. The virus was amplified in Vero cells for 3 passages, and 45-450 mL of measles virus seed stock (MV seed stock) were collected from the cell lysate of infected Vero cells. The viral titer of the virus seed stock was determined by a $TCID_{50}$ assay. The virus seed stock was divided into 1.0 or 4.5 mL aliquots and stored at <−60° C.

The titers of the MV-CEA p3 02-01 seed stock was $2.89 \times 10^7$ $TCID_{50}$/mL, and the MV-NIS p3 03-01 seed stock was $1.15 \times 10^7$ $TCID_{50}$/mL.

Example 2

GMP Manufacture of MV MVB from Lysates of Infected Cells

For the GMP manufacture of a measles virus, the measles virus stock (e.g., MVB) and cells (e.g., Master Cell Bank; MCB) used in the process should be free of microbiological and viral contaminants. To produce a MVB, a virus seed stock was amplified in cells from a MCB and the virus particles were harvested from the lysed cells. All steps were completed under GMP-compliant environmental conditions and practices. The manufactured MVB was tested and found to be free of adventitious agents before any clinical product manufactured from the MVB was released for use.

A Viral Vector Production Laboratory (VVPL) procedure for manufacturing a MV MVB using GMP is detailed below.

Reagents and Supplies

The following reagents and supplies were used in a GMP process to make a MV MVB: (1) a measles virus seed stock (e.g., a virus used to infect cells for production of the MVB), (2) WHO VERO MCB Cells, (3) VP-SFM (1×, liquid; e.g., a serum-free medium for growth of VERO cells for virus production), (4) VP-SFM with L-Glutamine (e.g., a serum-free medium for growth of VERO cells for virus production prepared from VP-SFM (1×, liquid) and L-Glutamine (200 mM)), (5) rProtease (e.g., recombinant protease), (6) Dulbecco's Phosphate Buffered Saline (D-PBS) without calcium and magnesium, and (7) Versene 1:5000 (1×, liquid; e.g., a solution of 0.2 g/L EDTA in PBS). The virus stock type varied according to the type of MV bank desired. For example, an MV-hCEA seed stock was used to make a MVB for measles virus containing a gene for human carcinoembryonic antigen (CEA).

Equipment and Instrumentation

The following reagents and supplies were used in a GMP process to make a MV MVB:

1. Certified SterilGARD III Advance Biosafety Cabinet, Class II Type B3; Cleanroom Class 100 (US Customary units)
2. Humidified Tissue Culture Incubators at 5% $CO_2$: ThermoForma Model 3950 Reach-In Incubator
3. Centrifuge/rotors: Sorvall Evolution Centrifuge with Sorvall SLC4000 rotor and Sorvall TC600 rotor.
4. Water bath, 37° C.
5. Calibrated pipettors (e.g., Rainin Distriman) for final filling of product vials.
6. Peristaltic pump suitable for pumping about 300 mL/min.
7. Insulated liquid nitrogen carrier(s).
8. Racks for 50 mL polypropylene conical tubes.
9. Racks for cryogenic vials (NNI#376589 or equivalent).
10. Cryogenic storage boxes, polycarbonate (NNI#5026-0909 and NNI#5027-0909 or equivalent).
11. Pipettors (e.g., pipetting aids) for serological pipettes.
12. Microscope.

Quality Control and Quality Assurance

All personnel contributing to the manufacture of a GMP product were fully trained and deemed competent in applicable GMP practices and in the tasks they performed. The VVPL GMP facility was cleaned and maintained to sustain the stipulated environmental conditions. The GMP facility was subjected to environmental monitoring to help ensure that conditions were satisfactory. All equipment and instrumentation was maintained, and maintenance was documented, according to written standard operating procedures and maintenance schedules. All aspects of the manufacturing process were documented as necessary, and documents were reviewed by the designated Quality Assurance representative. Necessary product testing and the criteria for satisfying testing specifications were stipulated prior to beginning the manufacturing run. The designated Quality Assurance representative reviewed all testing results and determined whether the product met the release specifications. MV clinical product prepared from a MV MVB was not released until Quality Assurance determined that the MV MVB met all release specifications.

Pre-Procedure

The VVPL Director specified the type and amount of measles virus MVB to be produced. Specifications were documented. The requisite Quality Control testing of the intermediate and final products were recorded. Product release criteria were predetermined and specified by the VVPL Director. Materials were ordered, received, inspected, managed, and transferred into the GMP Suite as needed. The Quality Assurance representative assigned a batch number to the manufacturing run which was used on documentation.

Procedure

All procedural steps manipulating the VERO MCB and measles virus in an open container during MV MVB preparation were performed in a biological safety cabinet. All waste was transported through the Exit Airlock (Hi-857B) into the Vestibule (Hi-857). All solid waste was decontaminated by steam sterilization. Liquid waste was either decontaminated by steam sterilization or treated with 10% bleach for at least one hour.

Stage 1: Thawing and Expansion of VERO Cells

WHO VERO MCB Cells were thawed and transferred to one or more T175 flasks. These MCB cells were expanded stepwise into multiple T500 flasks over the course of approximately 7-10 days. Expansion medium was VP-SFM with L-glutamine, without antibiotics. Each T500 flask of confluent VERO cells was expanded to a ten layer Cell Factory CF10 growth vessel. This resulted in one CF10 being seeded per flask of confluent VERO cells. A small proportion of one of the T500 flasks was also used to seed a T175 flask for an end-of-production cell control. The CF10 flasks were placed in 37° C. incubators until cells were grown to approximately 80% confluency, which typically took 3-6 days.

An end-of-production cell control was set up in a T175 flask using a 1:20 subculture from one of the T500 flasks being expanded to CF10s. The end-of-production cell T175 culture was maintained for two more subcultures (each at a 1:20 split). Upon reaching full confluency following the second subculture, this culture was examined under a microscope to look for the presence of any contaminants or cytopathic effect (CPE); then the culture was harvested. The majority of the cell culture supernatant was transferred to a labeled, sterile, 50 mL polypropylene tube, leaving about 3 mL of cell culture supernatant in the T175 flask. The cells were scraped off into the remaining 3 mL of cell culture supernatant and transferred to a separately labeled, sterile, 50 mL polypropylene tube. The end-of-production samples were placed in a sterile bag and transported to the pass-through in corridor 855E. The outside bag was wiped with alcohol wipes, and the package placed in the pass-through. A VVPL staff member removed the package of samples, transported it to the −80° C. freezer, and entered the samples into the freezer inventory.

Stage 2: Infection of VERO Cells in Cell Factories

All infecting information for the steps in Stage 2, including reagent lot numbers, was recorded. The appropriate MV seed stock was thawed, and its titer and amount was recorded on worksheet. Each CF-10 was infected with about $1 \times 10^8$ $TCID_{50}$ units of the MV seed stock. Based on an estimated cell number of $12 \times 10^9$ cells/CF10, the MOI was about 0.05-0.1 $TCID_{50}$ units per cell.

For each CF10, suspension of MV seed stock was prepared as follows: 250 mL VP-SFM with glutamine was aseptically pipetted or poured into a sterile, disposable 2 L Erlenmeyer flask; the appropriate volume of MV seed stock that contained $1 \times 10^8$ $TCID_{50}$ units was added to the bottle and mixed by swirling; the bottle was then capped aseptically with an autoclaved 2 L Feed cap.

Prior to infection, the culture media was aseptically removed from the CF10 and discarded; then the suspension of virus was added to the cell factory. The feed bottle used for virus addition was left attached.

The CF10 flasks were placed in a 37° C. $CO_2$ incubator for 2 hours, then one liter of VP-SFM with L-glutamine and without antibiotics was added to each CF10. The infected cell factories were then placed in a 32° C. $CO_2$ incubator for 72-96 hours or until the cells were >90% syncytia.

Stage 3: Harvesting MV from Cell Factories

The required amount of Versene and D-PBS was placed at room temperature the day before the harvest. Before the harvesting procedure, the water bath was allowed to equilibrate at 35-37° C. Completion of procedures in the production of MV MVB Bulk Product was documented.

Working with two CF10 flasks at a time, the cell culture supernatant was aseptically removed from the Cell Factories. Aliquots of the cell culture supernatant were saved in cryogenic vials for quality control testing when required. The volume of each aliquot was indicated in the GMP production plan. The aliquots were placed in a sterile bag. A VVPL staff member removed the sealed samples, transported them to the −80° C. freezer, and entered the samples into the freezer inventory. These samples were used for testing by the designated facility according to appropriate testing and/or sample handling procedures.

The remainder of the cell culture supernatant was discarded or processed separately as a pre-clinical virus batch. The cells attached to the CF10 were rinsed with 1 L of D-PBS without calcium and magnesium. The rinse solutions were then discarded. 400 mL of Versene were added to each CF10 and incubated for 10-30 minutes until the cell monolayer started to detach. The complete detachment of cells was aided by vigorous agitation. When cell detachment proceeded very slowly at room temperature (>20 minutes), placing the CF10 in a 37° C. $CO_2$ incubator aided cell detachment. The cell suspension was collected aseptically from each CF10 into sterile, disposable 1000 mL bottles. Each CF10 was rinsed with 500 mL of D-PBS without calcium and magnesium to collect remaining cells. This D-PBS rinse was pooled with the Versene cell suspension in the sterile, disposable 1000 mL bottles; a new 1000 mL bottle was used whenever the pooled suspension reached the 800 mL graduation mark. Multiple 800 mL aliquots of pooled cell suspension were collected as such.

The feed caps were removed from each 1000 mL disposable bottle containing cell suspension (circa 800 mL volume), and the contents of each bottle were aseptically poured into a 1 L centrifuge bottle. Filled centrifuge bottles were aseptically sealed with lids and placed in the pre-cooled Sorvall SLC4000 rotor while remaining CF10 flasks were harvested. For the final centrifuge bottle that may contain less than 800 mL of cell suspension, a balance bottle was created using the same volume of sterile D-PBS. The cell suspension was then centrifuged for 20 minutes at 3400 rpm (2000×g) and 4° C. using a Sorvall SLC4000 rotor in a Sorvall Evolution centrifuge. After centrifugation, supernatant was aseptically discarded into 2 L disposable Erlenmeyer flasks or any equivalent sterile container, and the cell pellet was resuspended in VP-SFM (without glutamine) using a volume corresponding to 40 mL per CF10. The cell suspension was divided into 20 mL aliquots in 50 mL conical tubes and subjected to two freeze/thaw cycles to lyse the cells. A complete freeze/thaw cycle included two steps: (1) the tubes were placed in liquid nitrogen for 5-10 minutes to snap freeze the cell suspension; and (2) the contents of the tubes were then thawed in a 37° C. water bath (for about 15-30 minutes). Cryoprotective gloves and glasses should be worn for protection during this procedure.

After the second freeze/thaw cycle, the cell lysate was frozen in liquid nitrogen. The frozen tubes were packaged by sealing in two layers of sterile bags. After transporting the sealed packages, the outside bag was wiped with alcohol wipes. A VVPL staff member removed the sealed intermediate product, transported it to the −80° C. freezer, and entered the intermediate product into the freezer inventory.

Stage 4: Clarification of the MV-Containing Cell Lysate

Before the clarification procedure, the water bath was allowed to equilibrate at 35-37° C. The intermediate product was removed from the −80° C. freezer and checked out from inventory. The outer bag was wiped with alcohol wipes and then the bag was removed. After the intermediate product was collected and transported to a viral production room, the remaining bag was removed and discarded. The tubes of cell lysate were thawed in a 37° C. water bath for 20-30 minutes to complete the third and final freeze/thaw cycle. The cell lysates were then clarified by centrifugation at 3400 rpm (2000×g), 20 min, and 4° C. using a Sorvall 600TC rotor in a Sorvall Evolution centrifuge.

Stage 5: Measles Virus MVB Bulk Product

The supernatants (i.e., clarified cell lysates (CCL)) were pooled aseptically in a 1000 mL sterile, disposable bottle or equivalent sterile container, and mixed. This clarified cell lysate was the MV MVB Bulk Product.

Aliquots were removed for MV MVB Bulk testing. Aliquots were labeled with the production batch number, "bulk product", the date, and the tech's initials; The labeled tubes containing aliquots of MV MVB Bulk Product for testing were wiped with alcohol wipes, and sealed in a sterile bag. The outside of the bag was wiped with alcohol wipes. A VVPL staff member removed the sealed package containing aliquots of MV MVB Bulk Product for testing, transported it to the −80° C. freezer, and entered the bulk (intermediate) product aliquots into the freezer inventory.

After testing aliquots had been removed, the bottle containing the remaining (i.e., major) portion of the MV MVB Bulk Product was wiped with alcohol wipes and sealed in a sterile bag to be transferred to the Filling Room.

Stage 6: Final Filling of Measles Virus MVB

The Measles Virus MVB Bulk Product (i.e., the volume remaining in the 1000 mL bottle) was transferred to the Filling Room. The package containing the MV MVB Bulk Product was wiped with alcohol wipes, the bag removed, and the container was transferred to the biological safety cabinet. All information for the final filling process was recorded on the MV MVB Final Fill Worksheet. The size and type of the vials used for the final product depended on the predetermined, desired product packaging. The planned number and size(s) of sterile vials were labeled with the name of the measles virus, the MVB lot number, the name and passage number of the seed stock from which the MVB was produced, the date of manufacture, the volume, and "Store at <−70° C."

Protective tape was applied to the vials to secure the printed label during freezing and storage. Fixed volumes of the MV MVB were aliquoted using an appropriate pipetting device into the labeled, sterile vials. The vials, which contained the MV MVB Final Product, were sealed by tightening the screw caps. The sealed and labeled vials were placed in a cryogenic vial box. The box was then placed in a sterile bag labeled with a Quarantine sticker and transported to the Ante Room. The cryogenic box containing the vials was transferred to a −80° C. freezer for quarantined storage. The required number of vials were removed and sent for testing as the MV MVB Final Vialed Product.

GMP Production Batch Summary

Product: MV-hCEA Measles Virus Master Virus Bank (MVB)

Batch Produced For: Master Virus Bank (MVB) of measles virus containing an h-CEA gene; the MV-CEA MVB to be used for future production of MV-CEA Clinical Product.

Bulk Product Vialed for Testing:
19 aliquots of 1.1 mL in 1.8 mL tubes
14 aliquots of variable vol. (per testing req.) in 15 mL tubes Final Product Vialed for Master Virus Bank:

26 aliquots of 1.1 mL in 1.8 mL tubes⇒volume=29 mL
87 aliquots of 4.5 mL in 4.5 mL tubes⇒volume=391 mL
1 aliquot of 1 mL in 4.5 mL tube⇒volume=1 mL
➔Total volume (final fill)=421 mL Titer of Final Product: $1.9 \times 10^7$ $TCID_{50}$ units/mL GMP Product Quality Control Testing Results
Production Process: MV-CEA Measles Virus Master Virus Bank

TABLE 1

| Assay | Bulk Product Specification | Bulk Product RESULT* | Vialed Product Specification | Vialed Product RESULT |
|---|---|---|---|---|
| Sterility | Pass | AppTec Study #01084 PASS | Pass | AppTec Study #01086 PASS |
| Bacteriostatic/Fungistatic Activity | Negative (Pass) | PASS | Negative (Pass) | PASS |
| Mycoplasma | Negative | Not Detected | | |
| 28-day In Vitro Adventitious Viruses: Vero cells | None Detected | None Detected | | |
| 28-day In Vitro Adventitious Viruses: MRC-5 cells | None Detected | None Detected | | |
| 28-day In Vitro Adventitious Viruses: A549 cells | None Detected | None Detected | | |
| In Vivo Adventitious Viruses: Embryonated chicken eggs | None Detected | None Detected | | |
| 28-day In Vivo Adventitious Viruses: Adult mice | None Detected | None Detected | | |
| 14-day In Vivo Adventitious Viruses: Suckling mice | None Detected | None Detected | | |
| Reverse Transcriptase Activity: PCR-based | Negative | Free of detectable Reverse Transcriptase activity | | |
| Bovine Viruses | None Detected | None Detected | | |
| Porcine Viruses | None Detected | None Detected | | |
| HIV-1 RT-PCR Assay | Negative | Not Detected | | |
| HIV-2 RT-PCR Assay | Negative | Not Detected | | |
| HTLV-I/II RT-PCR Assay | Negative | Not Detected | | |
| EBV PCR Assay | Negative | Not Detected | | |
| CMV PCR Assay | Negative | Not Detected | | |
| HHV-6 PCR Assay | Negative | Variant A: Not Detected Variant B: Not Detected | | |
| HHV-8 PCR Assay | Negative | Not Detected | | |
| Hepatitis B PCR Assay | Negative | Not Detected | | |
| Hepatitis C RT-PCR Assay | Negative | First Run: Interference Repeat: Not Detected | | |
| Human Polyoma Virus BKV and JCV PCR Assay | Negative | Negative | | |
| Human Parvovirus B19 PCR Assay | Negative | Not Detected | | |

TABLE 1-continued

|  | Bulk Product | | Vialed Product | |
|---|---|---|---|---|
| Assay | Specification | RESULT* | Specification | RESULT |
| AAV-2 | Negative | Not Detected | | |
| SRV PCR Assay | Negative | Not Detected | | |
| SV40 PCR Assay | Negative | Not Detected | | |
| STLV PCR Assay | Negative | Negative | | |
| SIV PCR Assay | Negative | Not Detected | | |
| SFV PCR Assay | Negative | Negative | | |
| Human CEA in culture supernatant | Present | Present (41,700 ng/mL) | | |
| MV-CEA N, M, H, F Proteins | | | Present/Correct Size | Present |
| Viral Genome Sequence: RT-PCR Sequencing | | | | Completed |
| Infectious Virus Concentration: $TCID_{50}$ Assay | | | | $1.9 \times 10^7$ $TCID_{50}$ units/mL |

Example 3

GMP Manufacture of MV Clinical Product from Supernatant of Infected Cells

MV Clinical Product (MV CP) is a high-titer measles virus preparation manufactured under current GMP, and can be used for clinical investigation.

To produce a MV CP, a MV MVB was amplified in VERO cells from a MCB and the virus was harvested from the supernatant of the infected cell culture. The cell culture supernatant containing the measles virus was pre-filtered to remove VERO cells, and then treated with Benzonase in the presence of magnesium chloride to digest contaminating nucleic acid. The MV in the treated cell culture supernatant was then concentrated and purified using tangential flow filtration and diafiltration. The concentrated and diafiltered measles virus was passed through a final clarifying filter prior to final vialing of the product as MV CP.

For the GMP manufacture of a MV CP, the MV stock (i.e., the MVB) and the MCB used in the process must be free of all microbiological and viral contaminants. The manufactured MVB used must be tested and found to be free of adventitious agents before any clinical product manufactured from that specific measles virus MVB can be released for use.

All procedural steps in the manufacture of MV CP were completed under GMP-compliant environmental conditions and practices. Samples from the manufacturing process were tested for sterility, identity, and for the presence of adventitious agents and must pass testing specifications before the MV CP was released for use in clinical studies.

A VVPL Procedure for the manufacture of a Measles Virus Clinical Product using GMP is detailed below. This procedure is applicable to production of small (e.g., <6 L) or large (e.g., up to 60 L) batches of MV CP. Any deviation from written procedure was documented. MV CP manufactured by this procedure is intended for use in Phase I/II clinical trials only.

Reagents and Supplies

The following reagents and supplies were used in a GMP process to make a MV CP: (1) a MV MVB (the specific MVB depends on the desired MV product); (2) WHO VERO MCB Cells; (3) VP-SFM with L-Glutamine (a serum-free medium for growth of VERO cells for virus production prepared from VP-SFM (1×, liquid) and L-Glutamine (200 mM); (4) rProtease; (5) Magnesium Chloride, 1.0 M; (6) D-PBS without calcium and magnesium; (7) water for Injection in a 20 L bag with luer connections; (8) Benzonase® Endonuclease (Purity Grade 1-Ultrapure Grade); and (9) 5% Sucrose, 50 mM Tris pH 7.4, and 2 mM $MgCl_2$ (custom-made by a CGMP manufacturer).

The following reagents and supplies also were used in a GMP process to make a MV CP: (10) tissue culture flasks (T75, T175 and T500); (11) sterile disposable serological pipettes; (12) sterile pipette tips (e.g., Rainin Distriman tips) for final filling of product vials; (13) disposable 1000 mL bottles, sterile (Nunc Nalgene #455-1000 or equivalent); (14) 15 mL polypropylene conical tubes, sterile; (15) 50 mL polypropylene conical tubes, sterile (Falcon #352098 or equivalent); (16) sterile bags (Fisher Whirl-Pak or equivalent); (17) internally threaded cryogenic vials for use as product vials, for example, 1.0, 1.8 and 4.5 mL sizes, sterile* (1.0 mL NNI#37724, 1.8 mL, NNI#377267 and 5 mL, NNI#379146 or equivalent); (18) fully assembled, sterile product vials, various sizes (e.g., Nalgene PETG diagnostic bottles); (19) final product vial labels; (20) alcohol wipes; (21) protective tape for securing product labels; (22) cell scrapers; (23) hollow fiber filter cartridge, 500 kD NMWCO assembled on the Flexstand tangential flow filtration apparatus complete with reservoir and flow path (Amersham/AGT Technologies), autoclaved; (24) feed/harvest lines, autoclaved (Luer fittings on tubing ends: male slip, male lock); (25) feed caps, 1 and 2 L, autoclaved; (26) harvest lines, autoclaved (Luer fittings on tubing ends: male lock, female lock); (27) male and female luer/plug assemblies, autoclaved (as a source of autoclaved male and female luer lock plugs); (28) filtration adapter, autoclaved (Luer fittings on tubing ends: male slip, female lock); (29) sterile bioprocess bags, various sizes; (30) gamma irradiated filter assembly with Pall 3 μm Versapor capsule filter; (31) gamma irradiated filter assembly with Pall, 1.2 μm serum capsule filter; (32) syringes, sterile, luer lock, various sizes; and (33) disposable Erlenmeyer flasks, 2 L, sterile (NNI#4112-2000).

Supplies specific to Cell Factory CF10 growth vessels included (a) Cell Factory CF10; (b) Vent Fitting for CF10, autoclaved; and (c) Media Fitting for CF10, autoclaved. Supplies specific to Cell Stack growth vessels include: (a) Cell Stack, ten-layer; (b) Filling Cap for Cell Stack; and (c) Vented Filling Cap for Cell Stack (optional).

Equipment and Instrumentation
1. Certified SterilGARD III Advance Biosafety Cabinet, Class II Type B3; Cleanroom Class 100 (US Customary units).
2. Humidified Tissue Culture Incubators at 5% $CO_2$: ThermoForma Model 3950 Reach-In Incubator.
3. Water bath, 37° C.
4. Pipettors for serological pipettes
5. Distriman pipette.
6. Calibrated pipettes.
7. Laboratory scale pump/pump heads; for example Masterflex Model 7523-60.
8. For large-scale production runs: Industrial process scale pump/pump heads; for example, Masterflex Model 77410-00.
9. AGT/Amersham Flexstand System for Tangential Flow Ultrafiltration.
10. Microscope.
11. Cryogenic storage boxes.
12. Racks for cryogenic vials.
13. Racks for 50 mL polypropylene tubes.
14. Plastic totes for transporting and storing filled bioprocess containers.
15. Plastic drum on dolly for holding 50 or 100 L bioprocess containers (BPC).

Quality Control and Quality Assurance

All personnel contributing to the manufacture of a GMP product were fully trained and deemed competent in applicable GMP practices and in the tasks they performed. The VVPL GMP facility was cleaned and maintained to sustain the stipulated environmental conditions. The GMP facility was subjected to environmental monitoring as required by the Environmental Monitoring Program for the GMP Suite of the VVPL to help ensure that conditions were satisfactory. Conditions that fell outside acceptable limits were addressed as prescribed by the Environmental Monitoring Program. All equipment and instrumentation were maintained, and maintenance was documented according to written standard operating procedures and maintenance schedules. All reagents and supplies used in a GMP process were selected, qualified and managed according to VVPL Procedure. All aspects of the manufacturing process were documented as necessary and the documents were reviewed by the designated Quality Assurance representative. When any deviations from procedure occurred or unexpected events arose during manufacture, a supervisor and Quality Assurance representative would be notified and the event documented. Necessary product testing and the criteria for satisfying testing specifications were stipulated prior to beginning the manufacturing run. The designated Quality Control representative reviewed all testing results and determined whether the product met the release specifications. MV CP prepared from a MV MVB was not released until Quality Assurance had determined that the MV MVB met all release specifications.

Pre-Procedure

The VVPL Director specified the type and amount of MV CP to be produced. The requisite Quality Control testing of the intermediate and final products was listed on the GMP Production Plan: Process Specifications and Product Quality Control Testing. Product release criteria were predetermined and specified by the VVPL Director. The GMP Production Process Component/Supply List Form was completed and approved for the planned manufacturing run. Materials were ordered, received, inspected, and managed according to VVPL Procedure. Materials were transferred into the GMP Suite as needed according to VVPL Procedure. The Quality Assurance representative assigned a batch number to the manufacturing run which was used on all documentation.

Procedure

All procedural steps manipulating the VERO MCB and measles virus in an open container during MV CP preparation were performed in a biological safety cabinet. All waste was transported through the Exit Airlock into the Vestibule. All solid waste was decontaminated by steam sterilization. Liquid waste was decontaminated either by steam sterilization or by treatment with 10% bleach for at least one hour.

Stage 1: Thawing and Expansion of VERO Cells

WHO VERO MCB Cells were thawed and transferred to one or more T175 flasks. These MCB cells were expanded stepwise into multiple T500 flasks over the course of approximately 7-10 days. Expansion media was VP-SFM with L-glutamine, without antibiotics. Each T500 flask of confluent VERO cells was expanded to a ten layer Cell Factory CF10. This resulted in one CF10 being seeded per flask of confluent VERO cells. A small proportion of one of the T500 flasks also was used to seed a T175 flask for an end-of-production cell control as described below. The CF10 flasks were placed in 37° C. incubators until cells were grown to approximately 80% confluency, which typically took 3-6 days.

An end-of-production cell control was set up in a T175 flask using a 1:20 subculture from one of the T500 flasks being expanded to CF10s. The end-of-production cell T175 culture was maintained for two more subcultures (each at a 1:20 split). Upon reaching full confluency following the second subculture, this culture was carefully examined under the microscope to look for the presence of any contaminants or CPE; then the culture was harvested. The majority of the cell culture supernatant was transferred to a labeled, sterile, 50 mL polypropylene tube, leaving approximately 3 mL of cell culture supernatant in the T175 flask. The cells were scraped off into the remaining 3 mL of cell culture supernatant and transferred to a separately labeled, sterile, 50 mL polypropylene tube. The end-of-production samples were placed in a sterile bag and transported to the pass-through. The outside of the bag was wiped with alcohol wipes and the package placed in the pass-through. A VVPL staff member removed the package of samples from the pass-through in the Entry Airlock, transported it to the −80° C. freezer, and entered the samples into the freezer inventory.

Stage 2. Infection of VERO Cells in Cell Factories

All infecting information for the steps in Stage 2, including reagent lot numbers, was recorded on the Measles Virus MVB Bulk Product Worksheet. The VVPL instructions for addition of measles virus MVB to the Cell Factory or Cell Stack were intended as guidelines. Alternate methods of aseptic addition might be acceptable providing they and the materials used were fully documented on the Measles Virus Clinical Product Worksheet.

The appropriate MV seed stock was thawed and its titer and amount was recorded on worksheet. Each CF-10 or Cell Stack was infected with approximately $1\times10^8$ $TCID_{50}$ units of the MV seed stock. Based on an estimated cell number of $1-2\times10^9$ cells/CF10, the MOI was about 0.05-0.1 $TCID_{50}$ units per cell.

When infecting in CF10 flasks, suspension of MV seed stock was prepared as follows: 250 mL VP-SFM with glutamine was aseptically pipetted or poured into a sterile, disposable 2 L Erlenmeyer flask; the appropriate volume of MV seed stock that contained $1\times10^8$ $TCID_{50}$ units was added to the bottle and mixed by swirling; the bottle was then capped aseptically with an autoclaved 2 L Feed cap. Alternatively, in order to collect infected cell culture supernatant in a bioprocess bag, the 2 L Erlenmeyer flask might be replaced by a 1 L sterile, disposable bottle and the 2 L feed cap might be replaced with a 1 L feed cap.

When infecting in Cell Stacks, MV MVB suspension for each Cell Stack was prepared as follows: 250 mL VP-SFM with glutamine was aseptically poured into a sterile, disposable 250 mL bottle or other equivalent container; the appropriate volume of MV MVB that contained $1 \times 10^8$ $TCID_{50}$ units was added to the bottle and mixed by swirling.

Prior to infection, the culture media were aseptically removed from the CF-10 or the Cell Stack; then the suspension of virus was added. The ten-layer flasks were placed in a 37° C. $CO_2$ incubator for 2 hours, with manual rocking to evenly distribute media at least once to prevent the cell layer from drying out. Then one liter of VP-SFM with glutamine and without antibiotics was added to each CF-10 or Cell Stack. The infected ten-layer culture vessels were placed in a 32° C. $CO_2$ incubator for 72(±6) hours. The date of infection was designated as Day 0.

Stage 3: Harvest of MV Bulk Clinical Product

The post-infection days chosen to be harvest days were determined from empirical observations during pre-clinical process development using that particular type of measles virus. For example, observations during process development for MV-CEA production indicated that Days 3, 4, 5, and 6 were optimal for harvesting cell culture supernatant. Experience with another MV type may indicate an alternative set of days as optimal for harvesting that virus.

Completion of the procedures for harvest of the MV Bulk Clinical Product was documented on the Measles Virus Clinical Product Worksheet (VVPL Form: F-A310VP). The MV Bulk Clinical Product was defined as the MV-containing cell culture supernatant recovered from the ten-layer flasks prior to further processing; this unprocessed MV-containing cell culture supernatant also contained any VERO cells which have detached during the infection.

The MV-containing cell culture supernatant was harvested from each ten-layer flask daily for three or four consecutive days. The first harvest typically was recovered from the ten-layer flasks approximately 72 hours following infection (e.g., on Day 3 following infection on Day 0). In general, harvests were taken on Days 3, 4, 5 and 6 following infection on Day 0. Except on the final day of harvest, the MV-containing cell culture supernatant removed from each ten-layer vessel was replaced with 1 L of fresh VP-SFM with L-Glutamine per vessel. Each daily harvest should result in an aseptic pool of the harvests from all the culture vessels processed on that day (e.g., the Day 3 harvest pool, the Day 4 harvest pool, etc.).

A sample of the MV-containing cell culture supernatant was taken from each daily harvest before any further processing of the harvest; the samples were stored at 2-8° C. (The volume of sample required, usually about 50 mL, was determined by the GMP Production Plan for the given production run). The method for sampling each daily harvest varied according to the type of container used for recovery of harvest pool. Typically, the daily harvest pool was collected in a sterile, bioprocess container, fitted with luer lock connections. Samples can be easily taken using a sterile syringe with a luer lock end and transferred to a sterile container for storage at 2-8° C. Alternatively, harvest pools collected in flasks or bottles can be sampled using sterile disposable serological pipettes. The details of the harvest procedure varied according to the use of CF10 flasks versus Cell Stacks, as well as, the number of CF10 flasks or Cell Stacks used. For guidance, some specific examples were included below (see Examples A and B).

Criteria to determine which harvests were processed for production were based on empirical observations of the percentage of cells exhibiting CPE (e.g., syncytia), the confluence and appearance of the infected cell monolayer, and the percentage of cells that had detached from the culture surface. Typically, harvests from Days 4, 5 and 6 were processed further to make the MV Clinical Product.

A sample of the MV Bulk Clinical Product was prepared by pooling the samples from the daily harvests chosen to undergo further processing to manufacture the clinical product, as follows. The samples from the daily harvest pools chosen for further processing were pooled in a suitably sized sterile container, for example, a 1000 mL, disposable bottle. Aliquots were removed for MV Bulk Clinical Product testing. Aliquots were labeled with the production batch number, "bulk product," the date, and the technicians' initials. The labeled tubes, containing aliquots of MV Bulk CP to be used for testing, were wiped with alcohol wipes and then sealed in a sterile bag. The sealed package was transported to the Corridor. The outside of the bag was wiped with alcohol wipes and the package placed in the pass-through connecting to the Entry Airlock. A VVPL staff member removed the sealed package containing the testing aliquots of MV Bulk CP from the pass-through in the Entry Airlock, transported the package to the −80° C. freezer, and entered the bulk product aliquots into the freezer inventory. Further processing of bulk clinical product was described beginning with Stage 4 below.

Example A

Procedure for a Daily Harvest from two CF10 Flasks i. Working with one CF10 flask at a time in the biosafety cabinet, transfer the feed/harvest line slip luer from the feed bottle to the female luer on a BPC (e.g., a 2 L BPC, or a 5 L BPC for Day 3 harvest). Set aside the male plug using aseptic technique.

ii. Pump the contents of the CF10 into the BPC using a lab scale peristaltic pump at speeds not exceeding 300 mL/min.

iii. When transfer of contents is complete, disconnect the slip luer of the feed/harvest line from the female luer on the bag. Re-plug the female luer on the bag with the saved male plug. Insert the slip luer of the feed/harvest line into the feed cap on a 1000 mL bottle containing 1 L of VP-SFM with L-Glutamine.

iv. Pump the VP-SFM with L-Glutamine into the CF10. Disconnect the CF10 from the pump and return the CF10 (with attached feed bottle) to the 32° C. incubator.

v. Repeat the procedure with the second CF10.

vi. Take a sample (volume determined from the Production Plan, usually 50 mL) from the BPC through the female luer on the bag using a 60 mL luer lock syringe. Recap the bag after sampling. Transfer the sample to a 50 mL tube; label the tube with the batch number, day of harvest (e.g., Day 3), date, techs initials and "Unprocessed Bulk" and store at 1-8° C. in the Cold Room in 855 G.

vii. Process the contents of the BPC as described in Stage 4 below.

Example B

Procedure for Daily Harvest from 20 Cell Stacks i. Working in the biosafety cabinet, connect the female lock luer of a harvest line (i.e., line has male lock luer on one end and female lock luer on the other to the male luer port of an empty, sterile, 25 L BPC that has been placed in a plastic tote. (Save the female plug from the BPC using aseptic technique, or plan to use one of the female caps from an autoclaved luer/plug assembly).

ii. Transfer a Cell Stack to the biosafety cabinet. Attach the male luer of the harvest line (already connected to the BPC) to the female luer fitting on the Cell Stack filling cap. (Save the male plug from the filling cap using aseptic technique, or plan to use one of the male caps from an autoclaved luer/plug assembly).

iii. Pump the contents of the Cell Stack into the BPC using a laboratory scale peristaltic pump at speeds not exceeding 600 mL/minute.

iv. When the Cell Stack is empty, transfer the male lock luer on the harvest line to the female luer on the next Cell Stack to be processed. The male plug from the second Cell Stack can be used to plug the filling cap on the first Cell Stack. Although only one Cell Stack is pumped at a time, having a second Cell Stack ready in the biosafety cabinet speeds up this procedure and facilitates making the aseptic connections. The verifier can transfer Cell Stacks between the incubator and the biosafety cabinet.

v. While the contents of the second Cell Stack are being pumped out, add 1 L of VP-SFM with L-glutamine to the first (i.e., emptied) Cell Stack as follows: unscrew the standard 33 mm vent cap from the second port of the Cell Stack; pour the contents of a 1 L bottle of VP-SFM with L-Glutamine into the Cell Stack; replace the vent cap.

vi. Repeat this procedure (Steps i through v) until all the Cell Stacks have been harvested and re-fed.

vii. After harvesting the final Cell Stack, the harvest line can be aseptically removed from the BPC and the male luer on the bag closed using a female plug.

viii. Take a sample (volume determined from the Production Plan, usually 50 mL) from the BPC through the female luer on the bag using a 60 mL luer lock syringe. Recap the bag after sampling. Transfer the sample to a 50 mL tube; label the tube with the batch number, day of harvest (e.g., Day 3), date, techs initials and "Unprocessed Bulk" and store at 1-8° C. in the Cold Room in 855 G.

ix. Process the contents of the 25 L bag as described in Stage 4 below.

Stage 4: Pre-Filtration and Benzonase Treatment of the MV Bulk Clinical Product

General overview: Each daily harvest pool chosen for further processing was treated on the day of harvest. Following harvest, the MV-containing cell culture supernatant, comprising the MV Bulk CP, was pre-filtered through a 3 µm filter to remove VERO cells. Then the filtered supernatant was treated with Benzonase (an endonuclease) to degrade any VERO cell DNA present. Following Benzonase treatment, the processed supernatant was stored at 2-8° C. until further purification into MV CP. For MV-CEA, data had shown that the harvest pools might be stored at 2-8° C. for at least 7-10 days without measurable loss of MV-CEA titer. When it is uncertain whether a given daily harvest pool would be chosen for further processing, it was processed as if it would be used for manufacture of the final product.

Pre-filtration: Daily harvest pools chosen for further processing were pre-filtered through a gamma-irradiated filter assembly containing a 3 µm Versapor capsule filter. For each of the harvest pools to be pre-filtered: (a) the male lock luer s on either end of a filter assembly were connected between the female luer of the daily harvest pool BPC and the female luer of an empty, sterile BPC of the same size; (b) full closure of the vent ports on the filter capsule was confirmed; and (c) the MV harvest pool was pumped through the 3 µm filter into the empty BPC using a lab-scale peristaltic pump at a speed preferably not exceeding 600 mL/min. The total volume that can be filtered through a single 3 µm filter depended on the amount of whole cells and cell debris in the cell culture supernatant. Conservatively, one filter should have the capacity to filter at least 10 L of MV Bulk CP. Therefore, for large harvest pools, it may be necessary to aseptically replace the filter with a fresh filter assembly part way through the filtration.

Benzonase treatment: For each BPC of pre-filtered supernatant, Benzonase was added to the pre-filtered MV-containing cell culture supernatant so that the final concentration of Benzonase was 20 Upper mL of cell culture supernatant (equivalent to 20,000 U Benzonase per L). The calculation for the amount of Benzonase used was documented on an MV CP Worksheet. To provide optimum conditions for Benzonase activity, sterile $MgCl_2$ was also added to the pre-filtered MV-containing cell culture supernatant to produce a final concentration of 2 mM $MgCl_2$ (for example, 2 mL of a 1 M solution of $MgCl_2$ was added per liter of cell culture supernatant). The calculation for the amount of $MgCl_2$ used was documented on the MV CP Worksheet. The Benzonase and $MgCl_2$ may be placed in a small volume of VP-SFM in a 1000 mL bottle. Benzonase was not placed directly into 1 M $MgCl_2$ (Ratio of VP-SFM to $MgCl_2$ solution should be at least 10:1). The Benzonase/$MgCl_2$/VP-SFM solution was pumped into the bag using a 1 L feed cap and a feed/harvest line. The filter assembly can be detached and discarded at the same time the Benzonase/$MgCl_2$ addition was made through the female luer on the BPC. Following the addition, the female luer on the BPC was plugged with a sterile male plug. The BPC was gently rocked by hand to mix the contents and then incubated at room temperature for 1 hour. The BPC was labeled with the production batch number, "Processed MV Bulk Clinical Product," the day of harvest (e.g., Day 3), the date, and the technician's initials. Following incubation, the BPC containing the "Processed MV Bulk Clinical Product" was transferred to the Cold Room and stored at 2-8° C. for at least 24 hours and up to 10 days prior to further purification.

Stage 5: Purification of MV Clinical Product

General Overview The MV CP was purified from the MV Bulk CP which had been pre-filtered and Benzonase-treated in the presence of $MgCl_2$. The purification process involved a multistage, tangential flow filtration process followed by a final polishing filtration step. The tangential flow filtration apparatus was based on the AGT/Amersham Flexstand System and incorporated an autoclavable, hollow-fiber, tangential flow filtration cartridge. First, the pre-filtered, Benzonase-treated bulk product was concentrated 5- to 10-fold to reduce the process volume. Second, the partially concentrated product was diafiltered against at least 5 volumes of Tris-buffered sucrose to simultaneously purify the measles virus and perform buffer exchange. Third, the purified measles virus was concentrated up to 50-fold compared to the bulk product. Finally, the concentrated, purified measles virus was filtered through a 1.2 µm Glass Fiber/Versapor filter as a final polishing step. This concentrated, purified, 1.2 µm-filtered measles virus was then transferred to the Filling Room for vialing as the final MV CP. The purification of MV for clinical product was documented on the MV CP Worksheet.

Preparation of the AGT/Amersham Flexstand Filtration System: the complete Flexstand system, comprised of stand, reservoir, cartridge, pressure gauges and tubing was fully sanitizable and autoclavable. A new set of flow path tubing was used for each GMP production run. The ultrafiltration cartridge was an appropriately sized, autoclavable, 500 kD NMWCO, AGT/Amersham hollow fiber tangential flow ultrafiltration cartridge selected for the MV purification process based on the volume of the production run (Table 2).

TABLE 2

| Total volume of "Processed Bulk Product" to be purified (L) | Cartridge Name | Recirculation rate corresponding to a shear of 4000 sec-1 (L/min) | Observed average permeate flux under standard operating conditions (mL/min) | MATS # of autoclaved Flexstand system prepared with this cartridge. |
|---|---|---|---|---|
| Less than 6 L | UFP-500-E-4X2MA | 1.2 | 30 | MS 03-0059 |
| 6-60 L | UFP-500-E-9A | 12.2 | 300 | MS 03-0060 |

In general, a new ultrafiltration cartridge was used for each GMP production batch; however, in some cases, a cartridge may be approved for re-use by QA depending on intended use and previous usage history (cartridges used in GMP processes may be sanitized, autoclaved, and re-used repeatedly for preclinical applications). The Flexstand system complete with cartridge was sanitarily prepared and autoclaved in preparation for use. The autoclaved Flexstand system was transported into the GMP Production Room.

The cartridge then was equilibrated. When equilibrating with VP-SFM (with or without L-Glutamine), 1 L of the VP-SFM may be added to the reservoir by means of a 1000 mL bottle, 1 L Feed Cap and a feed/harvest line (equilibration would generally be done in the Production Room, but could also be done in the Processing Room). Following equilibration, the Flexstand system was transported into the Processing Room. Aseptic connections between the containers of Processed Bulk Product and/or buffer and the Flexstand system were made in the biosafety cabinet in the Processing Room. The autoclaving procedure was scheduled such that the Flexstand system was used for the purification process within 48 hours of equilibrating the cartridge in VP-SFM post-autoclaving.

Tangential Flow Filtration: Initial concentration by; ultrafiltration: On the day of purification, the BPCs containing the "Processed MV Bulk CP" were removed from the cold room and placed at room temperature in the Processing Room. The aseptic connections used to attach the bags containing Processed MV Bulk Clinical Product to the reservoir of the Flexstand system varied according to the size of the production run and the type of containers that were used to collect the daily harvests of the Bulk Product. All aseptic connections were made in a biosafety cabinet. Depending on the size of the production batch, all of the Processed MV Bulk Product may be pumped into the reservoir before the ultrafiltration process was started or it may be pumped in continuously from connected BPCs as the initial step proceeds. The size of permeate container was determined by the size of the production batch; a 25 L BPC placed in a tote or a 100 L BPC placed in a drum on a dolly were common choices. Aseptic connections between the permeate line and the permeate container were made in a biosafety cabinet. Suitable parameters for tangential flow ultrafiltration include: a feed pressure of 4 psig or less; a retentate pressure ensuring that the transmembrane pressure drop was minimized and did not exceed 3 psig, assuming a permeate pressure of 0; and a recirculation rate corresponding to a shear rate of 4000 $sec^{-1}$ or less. During operation, factors such as temperature and viscosity of the process fluids would vary and it might be necessary to adjust the retentate pressure and/or the recirculation rate to maintain ideal operation conditions. The goal of the initial concentration step was to achieve a 5- to 10-fold concentration of the Processed Bulk Product prior to purification by diafiltration.

Tangential flow filtration: purification by diafiltration: The partially concentrated Processed Bulk Product was diafiltered against at least 5 volumes of 5% sucrose, 50 mM Tris, pH 7.4, 2 mM $MgCl_2$ (referred to as sucrose buffer). The BPCs containing the sucrose buffer were connected aseptically to the reservoir of the Flexstand by luer connections. Parameters for diafiltration were identical to those described for ultrafiltration above, except that during diafiltration, the flow of the sucrose buffer was matched to the permeate flow by controlling with a peristaltic pump and maintaining an approximately constant reservoir volume.

Tangential flow filtration: final concentration: After the diafiltration wash was completed, the partially concentrated and purified MV CP remaining in the reservoir was concentrated further by ultrafiltration. The MV was totally retained in the retentate. Ultrafiltration parameters were the same as described above. Concentration by ultrafiltration was continued until the retentate volume was approximately 1/50 of the starting volume of the Processed MV Bulk CP. It was not necessary to concentrate the retentate further than 1/50 the starting volume as further concentration had not been correlated with increased virus concentration in the final retentate. The retentate was aseptically recovered in a suitably sized sterile container, for example, a sterile disposable bottle or a sterile BPC with luer connections.

Final Polishing Step: 1.2 µm filtration: The container of MV-containing Final Retentate from the tangential flow process was aseptically disconnected from the Flexstand in the biosafety cabinet of the Processing Room and connected to a filter assembly containing a 1.2 µm serum filter capsule (Glass Fiber/Versapor). The filter assembly had two male luer lock fittings. Thus, connection to a feed cap would require a filtration adaptor. The downstream side of the filter assembly was either directly connected to an empty, sterile BPC or indirectly connected to a sterile bottle with a feed cap using a modified feed/harvest line. Using a peristaltic pump, the retentate was filtered through the 1.2 µm filter into the empty container at flow rates not exceeding 600 mL/minute. The retentate that had been filtered through the 1.2 µm filter was the "Purified MV CP." The container of Purified MV CP was aseptically disconnected from the filter assembly and sealed. The container was then wiped down with sterile alcohol wipes, placed in a sterile bag, and transferred to the Filling Room pass-through.

Specific examples of typical purifications, based on the volume of Processed MV Bulk CP, were given in the Examples C and D below.

Example C

Purification of 4 L of Processed MV Bulk CP i. The Bulk Product contained in two 2 L BPCs is pumped into the 5 L reservoir of a fully autoclaved and fully equilibrated Flexstand system containing a UFP-500-E-4X2MA cartridge.

ii. The initial (partial) concentration step results in a retentate of approximately 800 mL.

iii. The initial retentate is diafiltered against 4.0 L of sucrose buffer.

iv. The diafiltered retentate is then concentrated to a final volume of approximately 80-100 mL.

v. The final retentate is collected in a 1000 mL feed bottle via a feed/harvest line.

vi. The bottle containing the final retentate is connected to the 1.2 μm serum filter assembly via a modified feed/harvest line.

vii. The downstream end of the filter assembly is connected to a clean 1000 mL bottle using another modified feed/harvest line and a 1 L feed cap.

viii. The final retentate is pumped through the final 1.20 μm serum filter at a rate not exceeding 600 mL/min.

vi. Final volume after 1.2 μm filtration is approx 50-75 mL of Purified Measles Virus Clinical Product.

Example D

Purification of 60 L of Processed MV Bulk CP i. The Bulk Product is contained in three 25 L BPCs that are serially, aseptically, connected via luer connections to each other and the reservoir of a fully autoclaved and fully equilibrated Flexstand system containing a UFP-500-E-9A cartridge.

ii. Prior to the initial (partial) concentration step, approximately 5 L of Processed MV Bulk Product is pumped into the Flexstand 5 L reservoir.

iii. During this initial concentration step, Processed MV Bulk Product is pumped into the Flexstand reservoir at a rate which matches permeate withdrawal (approximately 300 mL/min).

iv. The initial (partial) concentration step results in a retentate of approximately 5-6 L being fully contained in the Flexstand reservoir.

v. The initial retentate is diafiltered against at least 30 L of sucrose buffer.

vi. The diafiltered retentate is then concentrated to a final volume of approximately 1.2 L.

vii. The final retentate is collected in a 2 L BPC connected to the sample collection port of the Flexstand.

viii. The 1.2 μm serum capsule filter assembly is connected between the female luers on the BPC containing retentate and a clean, empty 2 L BPC.

ix. The final retentate is pumped through the final 1.2 μm serum filter at a rate not exceeding 600 mL/min.

x. Final volume after 1.2 g/m filtration is approximately 1.2 L of Purified Measles Virus Clinical Product.

xi. Options for preparing for final vialing include: (1) pumping the contents of the BPC into sterile 1000 mL bottles from which product can be accessed with serological pipettes, or (2) withdrawing vialing aliquots from the BPC using a luer lock syringe and then placing product into intermediate containers prior to final vialing of small volumes.

Stage 6: Final Filling of Measles Virus Clinical Product

The Purified MV CP was transferred to the Filling Room pass-through from the Corridor and collected from the Filling Room side of the pass-through. The package containing the Purified MV CP was wiped with ethanol wipes, the bag removed, and the container was transferred into the biological safety cabinet. All information for the final filling process was recorded on the MV CP Final Fill Worksheet. The size and type of the vials used for the final product depended on the predetermined, desired product packaging. The planned number and size(s) of sterile vials were labeled with the name and lot number of the MV, the date of manufacture, the volume "Store at <−70° C.," "SINGLE USE ONLY," and "Caution: New Drug—Limited By Federal Law To Investigational Use."

Protective tape was applied to the labeled vials to secure the printed label during freezing and storage. Planned volumes of the MV CP were aliquoted using an appropriate pipetting device into the labeled, sterile vials. The vials, which then contained the MV CP, were sealed by tightening the screw caps. The filled vials containing MV CP were placed in a secondary container. For example, cryovials may be placed in a sterile 15 ml polypropylene tube. The vials enclosed in a secondary container were packaged by placing in a sterile bag or other closed storage container labeled with a Quarantine sticker and a sticker containing information identical to the vial label. Vials must remain quarantined until the MV CP lot is released by QA. The packaged vials were transferred to the −80° C. freezer in the Ante Room for quarantined storage. A GMP Product Inventory Log was initiated for the new product lot. The required number of vials were removed and sent for testing of the final vialed MV CP.

GMP Production Batch Summary

Product: MV-CEA Measles Virus Clinical Product

Batch Produced For: Clinical Product for Phase I Clinical Trial of Intraperitoneal Administration of a CEA-Expressing Derivative Manufactured from a Genetically Engineered Strain of Measles Virus in Patients with Cancer.

Bulk Product Vialed for Testing:
8 aliquots of 1.1 mL in 1.8 mL tubes
2 aliquots of 6 mL in 15 mL tubes
8 aliquots of 10 mL in 15 mL tubes Final Material Vialed for Clinical Product:
43 aliquots of 1.1 mL in 1.8 mL tubes⇒volume=47 mL
200 aliquots of 0.11 mL in 1.0 mL tubes⇒volume= 22 mL
➡Total volume (final fill)=69 mL Titer of Final Product: $4.0 \times 10^6$ $TCID_{50}$ units/mL GMP Product Quality Control Testing Results Production Process: MV-CEA Measles Virus Clinical Product

TABLE 3

| Assay | Bulk Product: Unprocessed Pooled Supernatant | | Vialed Product | |
|---|---|---|---|---|
| | Specification | RESULT | Specification | RESULT |
| Preliminary Sterility | No Growth | No Growth | No growth | No Growth |
| Sterility | Pass | Apptec Study #010240 PASS | Pass | Apptec Study #010244 PASS |
| Bacteriostatic/Fungistatic Activity | Negative | PASS | Negative | PASS |
| Mycoplasma | Negative | Not Detected | | |
| Bacterial Endotoxin | | | <1.0 EU/mL | 1.44 EU/mL |
| 28-day In Vitro Adventitious Viruses: Vero cells | None Detected | None Detected | | |
| 28-day In Vitro Adventitious Viruses: MRC-5 cells | None Detected | None Detected | | |
| 28-day In Vitro Adventitious Viruses: A549 cells | None Detected | None Detected | | |
| Human CEA | Present | Present (22,450 ng/mL) | | |
| Presence/Size of MV-CEA N, M, H, F Proteins | | | Present/Correct Size | Present |
| Total Protein Concentration: BCA method | | | ≦250 ug/ml | 207 μg/mL |
| Vero DNA Concentration: Picogreen assay | | | ≦200 ng/ml | <66.7 ng/mL |
| Vero DNA | Size range | Range from <50 base pairs to >23,000 base pairs | | |
| Size of Vero DNA: Agarose gel | | | ≦200 bp | Majority of DNA is <200 base pairs in size: 62% <200 bp and 38% from 200 to 400 bp |
| Benzonase Concentration ELISA/QPCR | | | ≦2 ng/ml | 1.36 ng/mL |
| Infectious Virus Concentration: $TCID_{50}$ assay | | | | $4.0 \times 10^6$ $TCID_{50}$ units/mL |
| Viral Genome Sequence: RT-PCR sequencing | | | | Completed |
| Virus Particle Concentration: QRT-PCR | | | | |

Clinical quality preparations of MV-NIS were produced by these methods but not using GMP.

Prep 1:

| | |
|---|---|
| Vector Construct | MV-NIS, MH-NIS (HP)3 |
| Production Cell Line | BioReliance Vero Cells |
| Product Description | Purified Pre-Clinical Product (p5) |
| Intended use | For pre-clinical studies |
| Storage Media | Sucrose buffer (5% sucrose, 50 mM Tris, 2 mM $MgCl_2$, pH 7.4) |
| Titer | $4.8 \times 10^7$ $TCID_{50}$ units/mL |
| Total Volume | 320 ml |
| Total Protein Concentration | 551.8 μg/mL |
| Total DNA Concentration (Vero Cell) | 370.1 ng/mL. |
| Benzonase concentration | 3.98 ng/mL |
| Sterility testing | No growth after 14 days in TSB (20-25° C.) or FTM (30-35°). |
| Storage Temperature | <−70° C. |
| Aliquot units | Amount vialed: 200 × 1.1 mL, 6 × 10 mL, 1 × 6 mL |

Prep 2:

| | |
|---|---|
| Vector Construct | MV-NIS, MH-NIS (HP)3 |
| Production Cell Line | BioReliance Vero Cells |
| Product Description | Purified Pre-Clinical Product (p5) |
| Intended use | For pre-clinical studies |
| Storage Media | Sucrose buffer (5% sucrose, 50 mM Tris, 2 mM $MgCl_2$, pH 7.4) |
| Titer | $3.5 \times 10^7$ $TCID_{50}$ units/mL |
| Total Volume | 850 ml |
| Total Protein Concentration | 646.6 μg/mL |
| Total DNA Concentration (Vero Cell) | 674.7 ng/mL. |
| Benzonase concentration | 3.26 ng/mL |
| Sterility testing | No growth after 14 days in TSB (20-25° C.) or FTM (30-35°). |
| Storage Temperature | <−70° C. |
| Aliquot units | Vialed: 300 × 1.1 mL, 6 × 10 mL, 100 × 4.5 mL, 1 × 6 mL |

Example 4

Production of Clinical Quality Paramyxoviridae Virus from Vero Cell Lysate

Vero cells are thawed, cultured, expanded, infected, and cultured with Paramyxoviridae viruses as described in Example 2. Vero cells are collected and lysed through three cycles of snap-freezing and thawing as also described in Example 2. The resulting cell lysate is clarified by centrifugation at 2000 g for 20 minutes at 4° C. (Sorvall 600TC rotor in a Sorvall Evolution centrifuge). The supernatants from each tube are pooled in a 1 L sterile disposable bottle and mixed with 20 U of a nuclease (Benzonase) per mL of supernatant. Clinical quality Paramyxoviridae Virus is produced from the virus obtained from the lysate using the techniques described in Example 3.

Example 5

Evaluation of Paramyxoviridae Virus Preparations

Clinical quality Paramyxoviridae virus that was purified from Vero cell culture supernatant was tested for the presence of microbes and impurities. The preparations were tested for the following: total protein, Vero cell DNA, and Benzonase®.

Paramyxoviridae virus bank product was tested for the presence of microbes, adventitious viruses, and specific viruses. No microbes or non-Paramyxoviridae viruses were found in any of the Paramyxoviridae virus preparations (Table 4). Impurities were present at extremely low concentrations (Table 4). Representative assays for each of the tests are provided in Table 5.

TABLE 4

Analysis of Paramyxoviridae virus preparations

| | Assay | MV-CEA Master Virus Bank: Bulk | MV-CEA Master Virus Bank: Vialed | MV-CEA Clinical Product: Bulk | MV-CEA Clinical Product: Vialed |
|---|---|---|---|---|---|
| Microbial Contaminants | Sterility | Pass | Pass | Pass | Pass |
| | Bacteriostatic/Fungistatic Activity | Negative | Negative | Negative | Negative |
| | Mycoplasma | Negative | | Negative | |
| | Bacterial Endotoxin | | | | <2.0 EU/ml |
| Adventitious Viruses | In Vitro 28-day: Vero cell line | None Detected | | None Detected | |
| | In Vitro 28-day: MRC-5 cell line | None Detected | | None Detected | |
| | In Vitro 28-day: A549 cell line | None Detected | | None Detected | |
| | In Vitro 28-day: NIH3T3 cell line | None Detected | | None Detected | |
| | In Vivo: Embryonated chicken eggs: yolk, allantoic | None Detected | | | |
| | In Vivo 28-day: Adult mice | None Detected | | | |
| | In Vivo 14-day: Suckling mice | None Detected | | | |
| | Reverse Transcriptase Activity: PCR-based | Negative | | | |
| Specific Viruses | In Vitro: Bovine Viruses | None Detected | | | |
| | In Vitro: Porcine Viruses | None Detected | | | |
| | AAV PCR Assay | Negative | | | |
| | HIV-1/2 PCR Assay | Negative | | | |
| | HTLV-I/II PCR Assay | Negative | | | |
| | EBV PCR Assay | Negative | | | |
| | CMV PCR Assay | Negative | | | |
| | HHV-6 PCR Assay | Negative | | | |
| | HHV-8 PCR Assay | Negative | | | |
| | Hepatitis B PCR Assay | Negative | | | |
| | Hepatitis C RT-PCR Assay | Negative | | | |
| | Human Polyoma Virus BKV and JCV PCR Assay | Negative | | | |
| | Human Parvovirus B19 PCR Assay | Negative | | | |
| | SRV PCR Assay | Negative | | | |
| | SV-40 PCR Assay | Negative | | | |
| | STLV PCR Assay | Negative | | | |
| | SIV PCR Assay | Negative | | | |
| | SFV PCR Assay | Negative | | | |
| Identity | Human CEA in culture supernatant | Present | | Present | |
| | Presence/Size of MV-CEA N, M, H, F Proteins | | Present/Correct Size | | Present/Correct Size |
| | Viral Genome Sequence: RT-PCR sequencing | | | | |
| Impurities | Total Protein Concentration: BCA method | | | | ≦250 ug/ml |
| | Vero DNA Concentration: Picogreen assay | | | | ≦200 ng/ml |
| | Size Vero DNA: Agarose and | | | | |

TABLE 4-continued

Analysis of Paramyxoviridae virus preparations

| | Assay | MV-CEA Master Virus Bank: Bulk | MV-CEA Master Virus Bank: Vialed | MV-CEA Clinical Product: Bulk | MV-CEA Clinical Product: Vialed |
|---|---|---|---|---|---|
| | Polyacrylamide Gels | | | | |
| | Benzonase Concentration: ELISA | | | | ≦2 ng/ml |
| Strength | Infectious Virus Concentration: TCID50 assay | | | | |

TABLE 5

Assays Used To Analyze Paramyxoviridae virus preparations

| | Assay | PERFORMED BY: AppTec Laboratory Services Catalogue number |
|---|---|---|
| Microbial Contaminants | Sterility | 30093 |
| | Bacteriostatic/Fungistatic Activity | or 30045 |
| | Mycoplasma | 30200 |
| | Bacterial Endotoxin | 30518 |
| Adventitious Viruses | In Vitro 28-day: Vero cell line | 37000/ |
| | In Vitro 28-day: MRC-5 cell line | 30841 |
| | In Vitro 28-day: A549 cell line | |
| | In Vitro 28-day: NIH3T3 cell line | |
| | In Vivo: Embryonated chicken eggs: yolk, allantoic | 30027 |
| | In Vivo 28-day: Adult mice | 30027.F |
| | In Vivo 14-day: Suckling mice | |
| | Reverse Transcriptase Activity: PCR-based | 30611 |
| Specific Viruses | In Vitro: Bovine Viruses | 30236 |
| | In Vitro: Porcine Viruses | 30129 |
| | AAV PCR Assay | 30762 |
| | HIV-1/2 PCR Assay | 30635 & 30623 |
| | HTLV-I/II PCR Assay | 30622 |
| | EBV PCR Assay | 30713 |
| | CMV PCR Assay | 30705 |
| | HHV-6 PCR Assay | 30719/30720 |
| | HHV-8 PCR Assay | 30702 |
| | Hepatitis B PCR Assay | 30703 |
| | Hepatitis C RT-PCR Assay | 30730 |
| | Human Polyoma Virus BKV and JCV PCR Assay | BioReliance subcontract |
| | Human Parvovirus B19 PCR Assay | 30619 |
| | SRV PCR Assay | 30797 |
| | SV-40 PCR Assay | 30715 |
| | STLV PCR Assay | BioReliance subcontract |
| | SIV PCR Assay | 30796 |
| | SFV PCR Assay | BioReliance subcontract VVPL: Assay Sensitivity |
| Identity | Human CEA in culture supernatant | 0.5 ng/mL |
| | Presence/Size of MV-CEA N, M, H, F Proteins | not applicable |
| | Viral Genome Sequence: RT-PCR sequencing | not applicable |
| Impurities | Total Protein Concentration: BCA method | 100 μg/mL |
| | Vero DNA Concentration: Picogreen assay | 1 ng/mL |
| | Size Vero DNA: Agarose and Polyacrylamide Gels | not applicable |
| | Benzonase Concentration: ELISA | 0.3 ng/mL |
| Strength | Infectious Virus Concentration: TCID$_{50}$ assay | 10 TCID$_{50}$ units/mL |

Determining Measles Virus Infectious Titer by the TCID$_{50}$ Method (5-fold Dilution Series) Using VERO Cells A parameter of a measles virus (MV) stock is the titer of infectious virus, i.e., the number of infectious units per unit volume. An infectious unit is the smallest amount of virus capable of producing a detectable biological effect in an assay. Replication of laboratory adapted and vaccine MV strains in VERO cells (African Green Monkey Kidney) produce a cytopathic effect, syncytia formation, which can be used to quantify the MV titer. The infectivity assay for determination of MV titers described herein is a quantal assay, i.e., an assay that detects the presence or absence of MV-induced syncytia in cell cultures infected with serial dilutions of the MV test sample. Syncytia in the cell cultures are detected by light microscopy. A 1/5 serial dilution series of each MV sample and a positive quantitative control are assayed in triplicate. The dilution of virus required to infect 50% of a given batch of cell cultures is defined as the tissue culture infective dose 50 (TCID$_{50}$). In this procedure, the TCID$_{50}$ is calculated using the Spearman Karber method. The MV infectious titer is reported as TCID$_{50}$ units/mL.

Bicinchoninic Acid (BCA) Protein Assay

In the Bicinchoninic Acid (BCA) protein assay, $Cu^{2+}$ ions form complexes with protein in alkaline solution. The complexed $Cu^{2+}$ is subsequently reduced to $Cu^{1+}$ by the protein components cysteine, cystine, tryptophan, tyrosine, and the peptide bond. The amount of reduction reflects the amount of protein present. BCA then complexes with $Cu^{1+}$ to form a purple-blue chromophore that absorbs at 562 nm. The protein concentration is proportional to absorbance at 562 nm. The calibration scheme in this procedure is set up to measure protein in the range of 100 to 1,000 μg/mL. When appropriate, this procedure may be used to assay samples containing ≧1,000 μg of protein/mL by analyzing dilutions of the sample. A BCA protein assay kit is available from Sigma (#BCA-1).

Quantitation of Benzonase® in Virus Preparations Using an ELISA Method

Benzonase® is a genetically engineered endonuclease produced in E. coli. Benzonase® hydrolyzes internal phosphodiester linkages between nucleotides in nucleic acids, including all types of DNA and RNA. Complete digestion of free nucleic acids by Benzonase® yields oligonucleotides of approximately 3 to 5 bases in length with a 5'-monophosphate terminus. Benzonase® is used in the Viral Vector Production Laboratory (VVPL) to degrade nucleic acids that originate from the cultured cells used to produce the virus. These nucleic acids are considered contaminants of the virus preparation. Following digestion of free DNA in the virus preparation with Benzonase®, the majority of the enzyme is removed by an ultrafiltration step. The amounts of residual Benzonase® and residual DNA in a virus preparation are measured to characterize the virus product. Benzonase® is analyzed using a commercially available Benzonase ELISA Kit developed by EM Industries, Inc Using this method, Benzonase is detectable at concentrations greater than 0.2 ng/mL. A Benzonase ELISA Kit is available from Merck KgaA (#1.01681.0002).

Quantitation of Double Stranded DNA Using the Picogreen dsDNA Quantitation Assay In the PicoGreen assay for measuring double-stranded DNA (dsDNA), PicoGreen, a proprietary cyanine dye, binds to DNA (and/or RNA) to form highly fluorescent complexes. PicoGreen alone is relatively non-fluorescent; however, its fluorescence is enhanced more than 1000-fold upon binding to dsDNA. Although PicoGreen also binds to single-stranded DNA (ssDNA) and to RNA, the level of fluorescence enhancement is significantly lower (<10%) for dye complexed with equimolar amounts of RNA, ssDNA, or oligonucleotides under the conditions of the assay, thus making it possible to quantify dsDNA in a heterogeneous nucleotide sample. The fluorescence of the PicoGreen-dsDNA complex is measured using a spectrofluorometer with an excitation wavelength of 480 nm and an emission wavelength of 520 nm. The concentration of dsDNA is proportional to the measured relative fluorescence intensity. Although the PicoGreen reagent can be used to measure dsDNA over a wide concentration range (25 pg/mL to 1000 ng/mL), the calibration scheme in this procedure is set up to measure dsDNA concentrations in the range of 10 to 250 ng/mL. When appropriate, this procedure may be used to assay samples containing $\geq$250 ng of DNA/mL by analyzing dilutions of the sample. A PicoGreen dsDNA Quantitation Assay Kit is available from Molecular Probes (P-11496).

Determination of Residual DNA Size Range

Virus preparations are produced in cultured cells and may be used for pre-clinical studies, or if produced under GMP, may be used for clinical trials. During certain production processes, Benzonase®, a genetically engineered endonuclease, is added to the cell culture supernatant or to the cleared cell lysate to degrade nucleic acids derived from the cultured cells. Benzonase® degrades all forms of DNA and RNA to yield nucleotides that are 3-5 bases in length. To ensure the effectiveness of the Benzonase® digestion step, pre- and post-enzyme treatment samples of the virus preparation are tested to determine the size range of the residual DNA. Prior to assay, the concentration of the residual DNA in the preparation is measured by the PicoGreen® DNA method (a separate assay procedure) to determine the amount of sample needed. Then to determine the DNA size range, residual DNA is extracted from samples of the virus preparation, and the extracted samples are analyzed by agarose gel electrophoresis (AGE) and polyacrylamide gel electrophoresis (PAGE). The migration of DNA molecules during electrophoresis is related to size (i.e., length in base pairs) of the molecules.

Example 6

GMP Manufacture of a MV MVB from Supernatants of Infected Cells

For the GMP manufacture of a measles virus, the measles virus stock (MVB) and the cells (MCB) used in the process must be free of all microbiological and viral contaminants.

The VVPL has two process options for manufacturing a MV MVB: (1) from the cleared cell-lysate of MV-infected cells, or (2) from the supernatant of MV-infected cell culture (i.e., this procedure). In both procedures a virus seed stock is amplified in cells from a MCB; however, in the cleared cell-lysate process, the virus particles are harvested from the lysed cells, while in the supernatant process, the virus particles are harvested from the supernatant of the MV-infected cell culture. In the supernatant process, the harvested supernatant is clarified using filtration to remove cell debris and is then designated as the MV MVB.

When the titer of a specific measles virus from supernatant harvest is sufficient for use as a MV MVB, manufacture of the MV MVB from supernatant is preferred for that virus due to the simpler procedure for preparing the MV MVB as compared to the cell lysate process.

All steps are completed under GMP-compliant (The VVPL complies with FDA Current Good Manufacturing Practice (CGMP) requirements to the extent they apply to an academic facility manufacturing biological products under an approved Investigational New Drug (IND) application for Phase I or Phase II clinical trials) environmental conditions and practices. The manufactured MVB must be tested and found to be free of adventitious agents before any clinical product manufactured from the Measles Virus MVB can be released for use.

A VVPL Procedure for the manufacture of a MV MVB from supernatant of MV-infected cells using GMP is detailed below.

Reagents and Supplies

The following reagents and supplies are used in a GMP process to make a MV MVB: (1) measles virus seed stock (a virus used to infect cells for production of the MVB; the virus stock type will vary according to the type of MV bank desired, such that an MV-hCEA seed stock will be used to make a MVB for measles virus containing a gene for human CEA, for example); (2) WHO VERO MCB Cells; (3) VP-SFM serum-free medium for growth of VERO cells for virus production (1×, liquid); (4) VP-SFM with L-Glutamine serum-free medium for growth of VERO cells for virus production prepared from VP-SFM (1×, liquid) and L-Glutamine (200 mM); (5) rProtease (recombinant protease); and (6) D-PBS without calcium and magnesium.

The following supplies and equipment also are used in a GMP process to make a MV MVB: (7) tissue culture flasks (T75, T175 and T500); (8) sterile disposable serological pipettes; (9) sterile pipette tips (e.g., Rainin Distriman tips) for final filling of product vials; (10) disposable 1000 mL bottle, sterile (Nunc Nalgene #455-1000 or equivalent.); (11) 15 mL polypropylene conical tubes, sterile; (12) 50 mL polypropylene conical tubes, sterile (Falcon #352098 or equivalent); (13) sterile bags (Fisher Whirl-Pak or equivalent); (14) internally-threaded, sterile, cryogenic vials (e.g., 1.0, 1.8, and/or 4.5 mL sizes) for use as sample or product vials; (15) final product vial labels; (16) alcohol wipes; (17) protective tape for securing product labels; (18) cell scraper; (19) feed/harvest lines, autoclaved (Luer fittings on tubing ends: male slip, male lock); (20) feed caps, 1 L, autoclaved; (21) feed caps, 2 L, autoclaved (optional); (22) harvest lines, autoclaved (Luer fittings on tubing ends: male lock, female lock); (23) male and female luer/plug or cap assemblies, autoclaved; (24) filtration adapter, autoclaved (Luer fittings on tubing ends: male slip, female lock) (optional); (25) sterile bioprocess bags, various sizes; (26) syringes, sterile, luer lock, various sizes; and (27) disposable Erlenmeyer flasks, 2 L, sterile (NNI#4112-2000 or equivalent; optional).

Supplies specific to Cell Factory CF10 growth vessels include (a) Cell Factory CF10; (b) Vent Fitting for CF10, autoclaved; and (c) Media Fitting for CF10, autoclaved. Supplies specific to Cell Stack growth vessels include (a) Cell Stack, ten-layer; (b) Filling Cap for Cell Stack; and (c) Vented Filling Cap for Cell Stack (optional).

Equipment and Instrumentation
1. Certified SterilGARD III Advance Biosafety Cabinet, Class II Type B3; Cleanroom Class 100 (US Customary units).
2. Humidified Tissue Culture Incubators at 5% $CO_2$: ThermoForma Model 3950 Reach-In Incubator.
3. Water bath, 37° C.
4. Pipettors for serological pipettes
5. Distriman pipette (optional)
6. Calibrated pipettes (optional)
7. Laboratory scale pump/pump heads; for example Masterflex Model 7523-60.
8. Microscope.
9. Cryogenic storage boxes for cryogenic vials and also for 15 mL and 50 mL polypropylene tubes.
10. Racks for cryogenic vials.
11. Racks and for 50 mL polypropylene tubes.
12. Racks for 15 mL polypropylene tubes.
13. Plastic totes for transporting and storing filled bioprocess containers.

Quality Control and Quality Assurance

All personnel contributing to the manufacture of a GMP product are fully trained and deemed competent in applicable GMP practices and in the tasks they perform. The VVPL GMP facility is cleaned and maintained to sustain the stipulated environmental conditions. The GMP facility is subjected to environmental monitoring as required by the Environmental Monitoring Program for the GMP Suite of the VVPL to help ensure that conditions are satisfactory. Conditions that fall outside acceptable limits are addressed as prescribed by the Environmental Monitoring Program. All equipment and instrumentation is maintained, and maintenance is documented, according to written standard operating procedures and maintenance schedules. All reagents and supplies used in a GMP process are selected, qualified and managed according to VVPL Procedure. All aspects of the manufacturing process are documented as necessary and the documents are reviewed by the designated Quality Assurance representative. If any deviations from procedure occur or unexpected events arise during manufacture, a supervisor and Quality Assurance representative are notified and the event is documented. Necessary product testing and the criteria for satisfying testing specifications are stipulated prior to beginning the manufacturing run. A designated Quality Control representative will review all testing results and determine whether the product meets the release specifications. MV Clinical Product prepared from a MV MVB is released only after Quality Assurance has determined that the MV MVB meets all release specifications.

Pre-Procedure

The VVPL Director specifies the type and amount of Measles Virus MVB to be produced. Specifications are documented on the GMP Production Plan: Process Specifications and Product Quality Control Testing. The requisite Quality Control testing of the intermediate and final products also is listed on the GMP Production Plan: Process Specifications and Product Quality Control Testing. Product release criteria are predetermined and specified by the VVPL Director. The GMP Production Process Component/Supply List Form is completed and approved for the planned manufacturing run. Materials are ordered, received, inspected, and managed according to VVPL Procedure. Materials are transferred into the GMP Suite as needed according to VVPL Procedure. A Quality Assurance representative assigns a batch number to the manufacturing run which is used on all documentation.

Procedure

All procedural steps manipulating VERO MCB and measles virus in an open container during MV MVB preparation are performed in a biological safety cabinet. All waste is transported through an Exit Airlock into the Vestibule. All solid waste is decontaminated by steam sterilization. Liquid waste is either decontaminated by steam sterilization or treated with 10% bleach for at least one hour.

Stage 1: Thawing and Expansion of VERO Cells

WHO VERO MCB cells are thawed and transferred to one or more T175 flasks. These MCB cells are expanded stepwise into multiple T500 flasks over the course of approximately 7-10 days. Expansion medium is VP-SFM with L-glutamine, without antibiotics. Each T500 flask of confluent VERO cells is expanded to a ten layer Cell Factory CF10. This results in one CF10 being seeded per flask of confluent VERO cells. A small proportion of one of the T500 flasks also are used to seed a T175 flask for an end-of-production cell control as described below. The CF10 flasks are placed in 37° C. incubators until cells are grown to approximately 80% confluency, which typically takes 3-6 days.

An end-of-production cell control is set up in a T175 flask using a 1:20 subculture from one of the T500 flasks being expanded to CF10s. The end-of-production cell T175 culture is maintained for two more subcultures (each at a 1:20 split). Upon reaching full confluency following the second subculture, this culture is carefully examined under the microscope to look for the presence of any contaminants or CPE; then the culture is harvested. The majority of the cell culture supernatant is transferred to a labeled, sterile, 50 mL polypropylene tube, leaving approximately 3 mL of cell culture supernatant in the T175 flask. The cells are scraped off into the remaining 3 mL of cell culture supernatant and transferred to a separately labeled, sterile, 50 mL polypropylene tube. The end-of-production samples are placed in a sterile bag and transported to the pass-through in corridor 855E. The outside of the bag is wiped with alcohol wipes and the package placed in the pass-through. A VVPL staff member removes the package of samples from the pass-through in the Entry Airlock, transports it to the −80° C. freezer, and enters the samples into the freezer inventory.

Stage 2: Infection of VERO Cells in Ten-Layer Culture Vessels

All infecting information for the steps in Stage 2, including reagent lot numbers, is recorded on a Bulk Product Worksheet. The appropriate MV seed stock is thawed and its titer and amount is recorded on worksheet. Each CF-10 or Cell Stack is infected with approximately $1\times10^8$ $TCID_{50}$ units of the MV seed stock. Based on an estimated cell number of $1-2\times10^9$ cells/CF10, the MOI is about 0.05-0.1 $TCID_{50}$ units per cell.

When infecting in CF10 flasks, suspension of MV seed stock is prepared as follows: 250 mL VP-SFM with glutamine is aseptically pipetted or poured into a sterile, disposable 2 L Erlenmeyer flask; the appropriate volume of MV seed stock that contains $1\times10^8$ $TCID_{50}$ units is added to the bottle and mixed by swirling; the bottle is then capped aseptically with an autoclaved 2 L feed cap. Alternatively, in order to collect infected cell culture supernatant in a bioprocess bag, the 2 L Erlenmeyer flask may be replaced by a 1 L sterile, disposable bottle and the 2 L feed cap may be replaced with a 1 L feed cap.

When infecting in Cell Stacks, MV MVB suspension for each Cell Stack is prepared as follows: 250 mL VP-SFM with glutamine is aseptically poured into a sterile, disposable 250 mL bottle or other equivalent container; the appropriate volume of MV MVB that contains $1 \times 10^8$ TCID$_{50}$ units is added to the bottle and mixed by swirling.

Prior to infection, the culture media is aseptically removed from the CF-10 or the Cell Stack; then the suspension of virus is added. The ten-layer flasks are placed in a 37° C. $CO_2$ incubator for 2 hours, with manual rocking to evenly distribute media at least once to prevent the cell layer from drying out. Then one liter of VP-SFM with glutamine and without antibiotics is added to each CF-10 or Cell Stack. The infected ten-layer culture vessels are placed in a 32° C. $CO_2$ incubator for 72(±6) hours. The date of infection is designated as Day 0.

Stage 3: Harvest of MV MVB Bulk Product

The post-infection days chosen to be harvest days are determined from empirical observations during pre-clinical process development using that particular type of measles virus. The MV MVB Bulk Product is defined as the MV-containing cell culture supernatant recovered from the ten-layer flasks prior to further processing; this unprocessed MV-containing cell culture supernatant also contains any VERO cells that have detached during the infection.

The MV-containing cell culture supernatant may be harvested from each ten-layer flask daily, typically for two to four consecutive days. The first harvest typically is recovered from the ten-layer flasks approximately 72 hours following infection (e.g., on Day 3 following infection on Day 0). Except on the final day of harvest, the MV-containing cell culture supernatant removed from each ten-layer vessel is replaced with 1 L of fresh VP-SFM with L-Glutamine per vessel. On each harvest day, the harvests from all culture vessels processed are pooled aseptically (e.g., the Day 3 harvest pool, the Day 4 harvest pool, etc.). A sample of the MV-containing cell culture supernatant is taken from each daily harvest pool before any further processing of the harvest; the samples are stored at 2-8° C. The volume of sample required, usually about 50 mL, is determined by the GMP Production Plan for the given production run. The method for sampling each daily harvest varies according to the type of container used for recovery of harvest pool. Typically, the daily harvest pool is collected in a sterile bioprocess container fitted with luer lock connections. Samples can be easily taken using a sterile syringe with a luer-lock end and transferred to a sterile container for storage at 2-8° C. Alternatively, harvest pools collected in flasks or bottles can be sampled using sterile disposable serological pipettes. The details of the harvest procedure will vary according to the use of CF10 flasks versus Cell Stacks, as well as the number of CF10 flasks or Cell Stacks used. For guidance, an example is provided below (see Example E).

Criteria to determine which harvests will be processed further are based on empirical observations of the percentage of cells exhibiting CPE (cytopathic effects such as syncytia), the confluence and appearance of the infected cell monolayer, and the percentage of cells that have detached from the culture surface. Typically, harvests from Days 4 and/or 5 are processed further to make the MV MVB.

After the final harvest, the pool samples from the daily harvests to be processed to manufacture the final MV MVB are combined to make a sample representative of the MV MVB Bulk Product. The samples from the daily harvest pools chosen for further processing are combined in a suitably sized sterile container, for example a 1000 mL disposable bottle, and mixed by gentle swirling. Required testing for the bulk product is listed in the GMP Production Plan; the aliquots for testing are removed from the bulk product sample. Aliquots are labeled with the production batch number, "bulk product", the date, and the technicians' initials. The labeled tubes, containing aliquots of MV MVB Bulk Product to be used for testing, are wiped with alcohol wipes and then sealed in a sterile bag. The sealed package is transported to the Corridor, where the outside of the bag is wiped with alcohol wipes and the package is placed in the pass-through connecting to the Entry Airlock. A VVPL staff member removes the sealed package containing the testing aliquots of MV MVB Bulk Product from the pass-through in the Entry Airlock, transports the package to the ultra-low freezer, and enters the bulk product aliquots into the −80° C. freezer inventory. Further processing of MV MVB Bulk Product is described beginning with Stage 4 below.

Example E

Procedure for Daily Harvest from Multiple Cell Stacks i. Working in the biosafety cabinet, connect the female lock luer of a harvest line (i.e., line has male lock luer on one end and female lock luer on the other) to the male luer port of an empty, sterile, appropriately sized BPC that has been placed in a plastic tote. Save the female plug from the BPC using aseptic technique, or plan to use one of the female caps from an autoclaved luer/plug assembly.

ii. Transfer two Cell Stacks to the biosafety cabinet. Attach the male luer of the harvest line (already connected to the BPC) to the female luer fitting on the filling cap of the first Cell Stack to be processed. Save the male plug from the filling cap using aseptic technique, or plan to use one of the male caps from an autoclaved luer/plug assembly.

iii. Pump the contents of the Cell Stack into the BPC using a laboratory scale peristaltic pump at speeds not exceeding 600 mL/min.

iv. When the Cell Stack is empty, transfer the male lock luer on the harvest line to the female luer on the next Cell Stack to be processed. The male plug from the second Cell Stack can be used to plug the filling cap on the first Cell Stack. Although only one Cell Stack is pumped at a time, having a second Cell Stack ready in the biosafety cabinet will speed up this procedure and facilitate making the aseptic connections. The verifier can transfer Cell Stacks between the incubator and the biosafety cabinet.

v. While the contents of the second Cell Stack are being pumped out, add 1 L of VP-SFM with L-glutamine to the first (i.e., emptied) Cell Stack, as follows: unscrew the standard 33 mm vent cap from the second port of the Cell Stack; pour the contents of a 1 L bottle of VP-SFM with L-Glutamine into the Cell Stack; replace the vent cap.

vi. Repeat this procedure (Steps i. through v.) until all the Cell Stacks have been harvested and re-fed.

vii. After harvesting the final Cell Stack, the harvest line can be aseptically removed from the BPC and the male luer on the bag closed using a female plug.

viii. Take a sample (volume determined from the Production Plan, usually 50 mL) from the BPC through the female luer on the bag using a 60 mL luer lock syringe. Recap the bag after sampling. Transfer the sample to a 50 mL tube; label the tube with the batch number, day of harvest (e.g., Day 3), date, techs initials and "Unprocessed Bulk" and store at 2-8° C.

ix. Process the contents of the BPC as described in Stage 4 below.

Stage 4: Clarification of the MV MVB Bulk Product

General overview: Each daily harvest pool intended for further processing is filtered on the day of harvest. Following harvest, the MV-containing cell culture supernatant, comprising the MV MVB Bulk Product, is pre-filtered through a 3 µm filter to remove VERO cells. The filtered supernatant is stored at 2-8° C. or pooled immediately with other filtered harvest pools to create the MV MVB Final Product. For MV-CEA and MV-NIS, data has shown that the filtered harvest pools may be stored at 2-8° C. for at least 7-10 days without measurable loss of viral titer. Typically a day 3 harvest is not processed further.

Clarification of MV MVB bulk product by filtration: Daily harvest pools chosen for further processing are filtered through a gamma-irradiated filter assembly containing a 3 g/m Versapor capsule filter. For each of the harvest pools to be filtered: (a) the male lock luers on either end of a filter assembly are connected between the female luer of the daily harvest pool BPC and the female luer of an empty, sterile BPC of the same size; (b) full closure of the vent ports on the filter capsule is confirmed; (c) the MV harvest pool is pumped through a 3 µm filter into an empty BPC using a lab-scale peristaltic pump at a speed preferably not exceeding 600 mL/min; (d) the total volume that can be filtered through a single 3 µm filter depends on the amount of whole cells and cell debris in the cell culture supernatant (conservatively, one filter should have the capacity to filter at least 10 L of MV MVB Bulk Product); (e) the BPC containing the filtered MV MVB Bulk Product is labeled with the production batch number, "Processed MV MVB Bulk," the day of harvest (e.g., Day 4), the date, and the technicians' initials; and (f) the BPC containing the Processed MV MVB Bulk may be pooled immediately with other processed harvests as described in Stage 5 below, or transferred to a Cold Room and stored at 2-8° C. for up to 10 days prior to pooling and vialing. Alternate procedures for filtering of the MV MVB Bulk product from 1000 mL bottles or 2 L flasks into empty, sterile BPC or flasks using a filter assembly, feed caps and filter adaptors are also acceptable, providing that they are fully documented and aseptic conditions are maintained.

Stage 5: Pooling of the Processed MV MVB Bulk Product to make Measles Virus MVB Final Product On the day of final filling, the containers of Processed MV MVB Bulk are removed from the cold room and transferred to a biosafety cabinet in the Processing Room. The containers of Processed MV MVB Bulk are aseptically combined in a single BPC or flask to create a single pool; this is the MV MVB Final Product.

The aseptic connections used during the pooling of the Processed MV MVB bulk depend on the type of containers used. For example, 2×2 L pools of Day 4 and Day 5 Processed MV MVB Bulk contained in 2 L BPCs may be pumped into an empty, sterile 5 L BPC using direct connection between the bags or via a feed harvest line. Uniform mixing of the MV MVB Final Product is accomplished by gently rocking or swirling the BPC or flask.

To facilitate final vialing, the MV MVB Final Product is pumped into empty, sterile 1000 mL bottles or 2 L Erlenmeyer flasks using a feed harvest line and appropriately sized feed caps. The bottles or flasks containing the MV MVB Final Product are labeled with the production batch number, "MV MVB Final Product," the date and the technicians' initials. The bottles or flasks containing the MV MVB Final Product are wiped down with sterile alcohol wipes, each placed in a sterile bag, and transferred to the Filling Room pass-through.

Stage 6: Final Filling of Measles Virus MVB Final Product

The MV MVB Final Product is transferred to the Filling Room pass-through from the Corridor and collected from the Filling Room side of the pass-through. The package containing the MV MVB Bulk Product is wiped with alcohol wipes, the bag removed, and the container is transferred to a biological safety cabinet.

The size and type of the vials or tubes used for the final product depend on the predetermined, desired product packaging. The planned number and size(s) of sterile vials or tubes are labeled with the name of the MV, the MVB lot no., the name and passage number of the seed stock from which the MVB was produced, the date of manufacture, the volume, and "Store at <−70° C."

Protective tape is applied to the vials to secure the printed label during freezing and storage. Planned volumes of the MV MVB are aliquoted using an appropriate pipetting device into the labeled, sterile vials or tubes. The vials or tubes, now containing the MV MVB Final Product, are sealed by tightening the screw caps. The sealed and labeled vials are placed in a cryogenic vial or tube box(es), placed in a sterile bag labeled with a Quarantine sticker, and transported to the Ante Room. The cryogenic box(es) containing the vials or tubes is(are) transferred to an ultra-low freezer in the Ante Room for quarantined storage at −80° C. The required number of vials and/or tubes are removed and sent for testing of the MV MVB Final Vialed Product.

Example 7

Summary of Production Process for MV-NIS MVB

Cell Expansion One or two vials of BioReliance/WHO VERO MCB are thawed and expanded to two, ten-layer Corning Cell Stacks (CS10) in VP-SFM serum-free media at 37° C., 5% $CO_2$ until cell monolayers are approximately 90% confluent.

Infection (Day 0): The circa 90% confluent VERO cell monolayers in the ten-layer Cell Stacks will are infected with the MV-NIS p3 Seed Stock at a multiplicity of infection of 0.01 $TCID_{50}$/cell for 2 hours at 37° C., 5% $CO_2$. Fresh growth medium (one liter per CS10) is added and the cultures incubated at 37° C., 5% $CO_2$. The CPE of MV infection is monitored daily.

Harvest of MV-NIS MVB Bulk: Infected cell supernatants are collected from each CS on days 3, 4, and 5 post-infection to create a daily harvest pool. A sample of each daily harvest pool is taken prior to further processing. After collecting the supernatants on days 3 and 4, fresh growth medium (one liter per CS) is added and incubation of the cultures continued at 37° C., 5% $CO_2$. The MV-containing cell culture supernatant is the MV-NIS Bulk Product.

Processing ("purification") of MV-NIS MVB Bulk: On the day of harvest, each daily pool of MV-NIS MVB Bulk (circa 2 liters each) is filtered through a 3 µm Versapor pre-filter to remove any intact VERO cells, and is stored at 2-8° C. After the final harvest, the harvest pool samples from the daily harvests processed and pooled to create the final MVB and then combined to make a sample representative of the MV-NIS Bulk Product. The MV-NIS MVB Bulk sample is used for bulk product release testing.

Pooling of Processed Bulk to make MV-NIS MVB Final Product: The Processed Bulks from the two days where the cell cultures displayed extensive CPE and the majority of the VERO cells are still attached to the CSs are pooled. Based on previous MV-NIS virus production experience, the Processed Bulk from days 4 and 5 are used to create a circa 4 L pool of MV-NIS MVB Final Product.

Filling of MV-NIS MVB Final Product: The MV-NIS MVB Final Product is then aliquoted aseptically into approved vials, about 120 vials of 30 mL and 40 vials of 10 mL, and stored at <−65° C. Aliquots of the MV-NIS MVB vialed product are used for release testing.

Non-GMP Example Data:

A total of 1880 mL MV-NIS p4 2004 01A MVB was vialed. Samples stored at <−60° C.

TABLE 6

Number of vials and vial content volume.

| Vialing volume | Number of vials filled |
| --- | --- |
| 1 mL | 50 |
| 2 mL | 50 |
| 5 mL | 28 |
| 10 mL | 39 |
| 40 mL | 30 |

Titer: $4.53 \times 10^6$ TCID$_{50}$ units/mL

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for making a composition comprising measles virus, wherein said composition has a volume greater than 300 mL and a measles virus titer greater than $10^6$ TCID$_{50}$ per mL said method comprising:
    (a) obtaining a sample of measles virus in serum-free medium,
    (b) pre-filtering said sample to obtain a pre-filtered product,
    (c) subjecting said pre-filtered product to a hollow fiber tangential flow filtration process to obtain a concentrated, purified measles virus product, and
    (d) subjecting said concentrated, purified measles virus product to a polishing filtration step to form said composition.

2. The method of claim 1, wherein said serum-free medium has a volume between 10 L and 100 L.

3. The method of claim 1, wherein said serum-free medium has a volume between 30 L and 200 L.

4. The method of claim 1, wherein said serum-free medium has a volume between 60 L and 200 L.

5. The method of claim 1, wherein said composition has a measles virus titer between $10^6$ TCID$_{50}$ per mL and $10^{15}$ TCID$_{50}$ per mL.

6. The method of claim 1, wherein said composition has a measles virus titer between $10^9$ TCID$_{50}$ per mL and $10^{15}$ TCID$_{50}$ per mL.

7. The method of claim 1, wherein the virus in step (a) was replicated in a cell selected from the group consisting of a Vero cell, Vero-αHis cell, HeLa cell, HeLa-S3 cell, 293 cell, PC12 cell, CHO cell, 3T3 cell, or a combination thereof.

8. The method of claim 1, wherein the virus in step (a) was replicated in a Vero cell.

9. The method of claim 8, wherein said Vero cell is cultured in a multi-layered dish.

10. The method of claim 8, wherein said Vero cell is cultured in a microcarrier.

11. The method of claim 5, wherein said Vero cell is cultured at a temperature between about 30° C. and about 33° C.

12. The method of claim 1, wherein said method comprises after step (a), contacting said sample with an enzyme.

13. The method of claim 12, wherein said enzyme is an endonuclease.

14. The method of claim 1, wherein said composition is sterile.

* * * * *